United States Patent
Iwasaki et al.

(10) Patent No.: US 11,946,975 B2
(45) Date of Patent: Apr. 2, 2024

(54) MAGNETIC SENSOR AND INSPECTION DEVICE

(71) Applicant: KABUSHIKI KAISHA TOSHIBA, Tokyo (JP)

(72) Inventors: Hitoshi Iwasaki, Nerima Tokyo (JP); Satoshi Shirotori, Yokohama Kanagawa (JP); Akira Kikitsu, Yokohama Kanagawa (JP); Yoshihiro Higashi, Komatsu Ishikawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 142 days.

(21) Appl. No.: 17/445,684

(22) Filed: Aug. 23, 2021

(65) Prior Publication Data
US 2022/0214401 A1 Jul. 7, 2022

(30) Foreign Application Priority Data
Jan. 4, 2021 (JP) ................................ 2021-000054

(51) Int. Cl.
  *G01R 31/382* (2019.01)
  *A61B 5/245* (2021.01)
  *G01N 27/90* (2021.01)
(52) U.S. Cl.
  CPC ....... *G01R 31/382* (2019.01); *G01N 27/9006* (2013.01); *A61B 5/245* (2021.01)
(58) Field of Classification Search
  CPC ...... G01R 31/382; G01R 33/02; A61B 5/245; G01N 27/9006; G01C 17/28;
(Continued)

(56) References Cited

U.S. PATENT DOCUMENTS

2006/0072249 A1\* 4/2006 Wakui .................. G01R 33/093
  257/E27.005
2018/0271395 A1 9/2018 Iwasaki et al.
(Continued)

FOREIGN PATENT DOCUMENTS

JP 2018-155719 A 10/2018
JP 2019-45496 A 3/2019
(Continued)

*Primary Examiner* — Lee E Rodak
*Assistant Examiner* — Trung Q Nguyen
(74) *Attorney, Agent, or Firm* — Finnegan, Henderson, Farabow, Garrett & Dunner, LLP

(57) ABSTRACT

According to one embodiment, a magnetic sensor includes a first sensor part. The first sensor part includes a first magnetic member, a first counter magnetic member, and a first magnetic element. A direction from the first magnetic member toward the first counter magnetic member is along a first direction. The first magnetic element includes one or a plurality of first extension parts. The first extension part includes a first magnetic layer, a first counter magnetic layer, and a first nonmagnetic layer. The first magnetic layer includes a first portion, a first counter portion, and a first middle portion. A direction from the first portion toward the first counter portion is along the first direction. The first middle portion is between the first portion and the first counter portion. The first nonmagnetic layer is between the first counter magnetic layer and at least a portion of the first middle portion.

19 Claims, 20 Drawing Sheets

(58) Field of Classification Search
CPC ............ H04M 1/0277; H04M 2250/12; H05K
1/181; H05K 9/0026; H05K 9/0075
USPC .............. 324/430–435, 200, 207.14–207.18,
324/219–225, 239, 241, 637–639, 600,
324/500, 529, 530, 764.01, 134
See application file for complete search history.

(56) References Cited

U.S. PATENT DOCUMENTS

| | | |
|---|---|---|
| 2019/0369172 A1 | 12/2019 | Kikitsu et al. |
| 2020/0319269 A1 | 10/2020 | Shirotori et al. |
| 2021/0080519 A1 | 3/2021 | Iwasaki et al. |

FOREIGN PATENT DOCUMENTS

| | | |
|---|---|---|
| JP | 2019-132719 A | 8/2019 |
| JP | 2019-207167 A | 12/2019 |
| JP | 2020-170838 A | 10/2020 |
| JP | 2021-47169 A | 3/2021 |

* cited by examiner

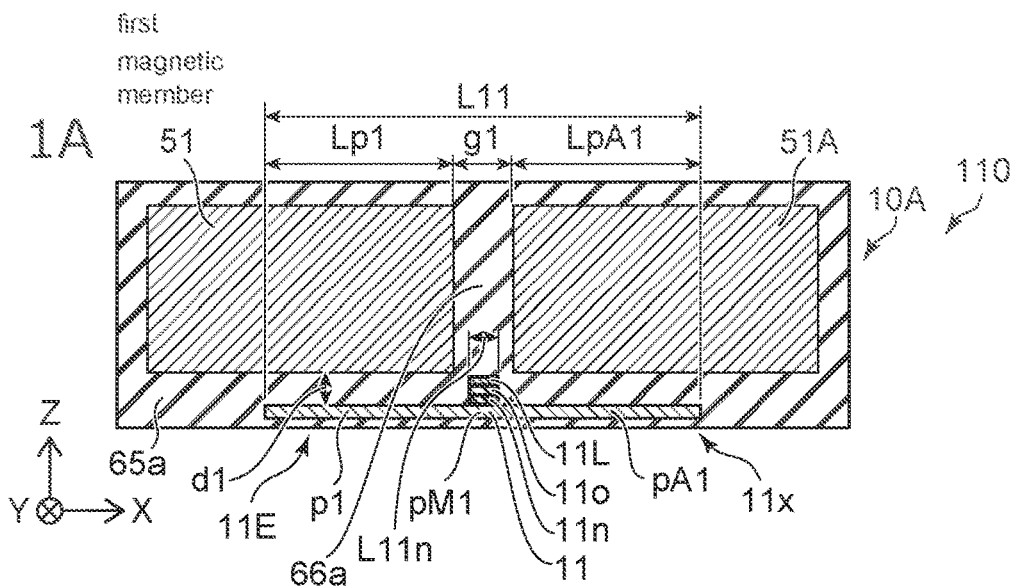
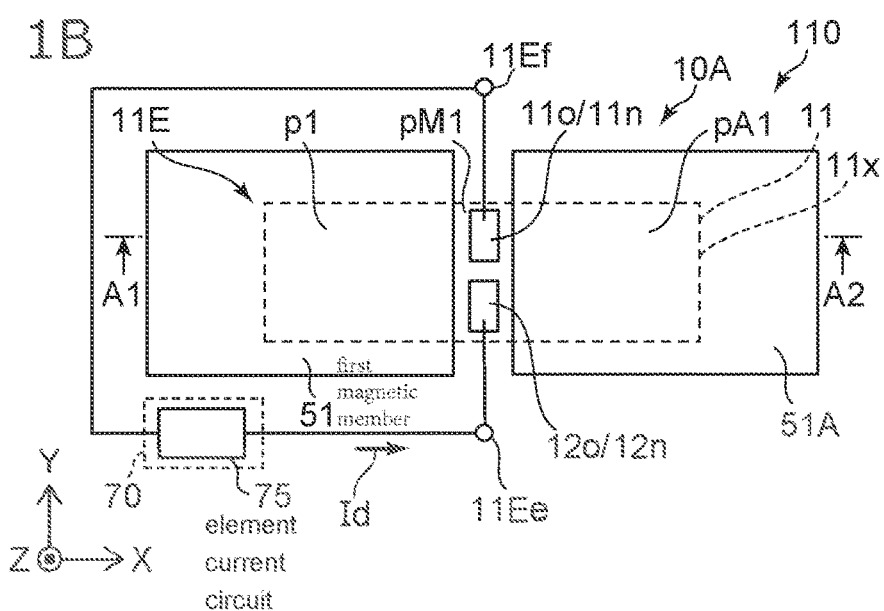
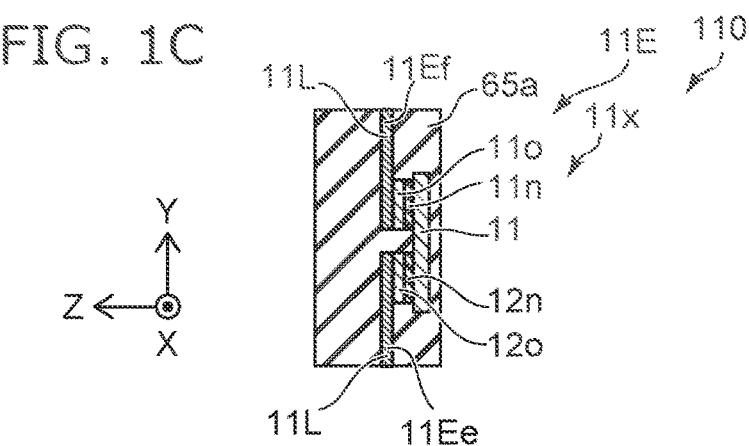

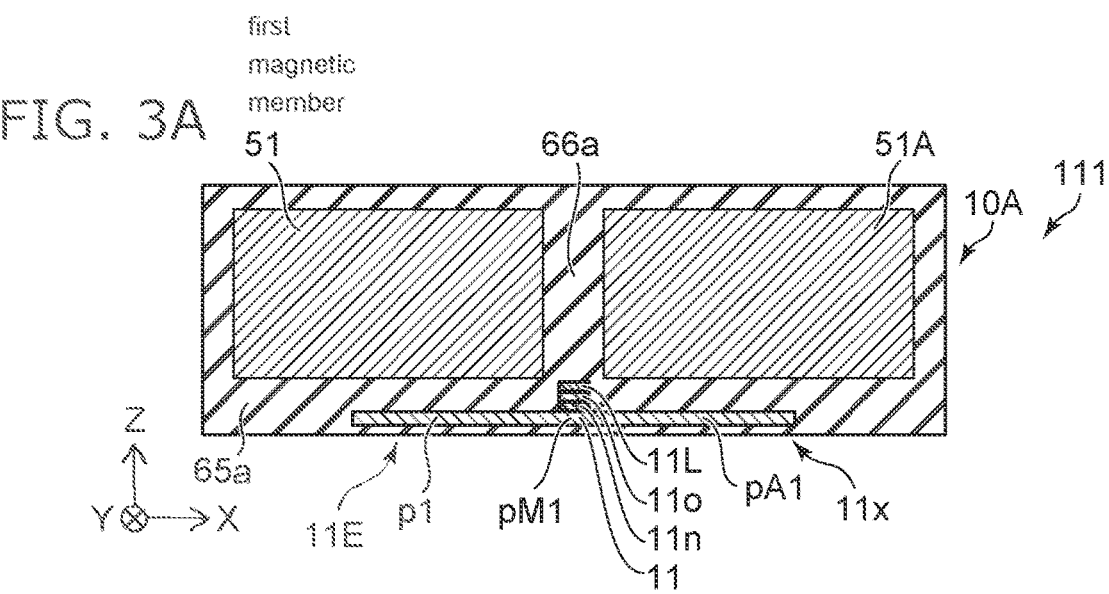
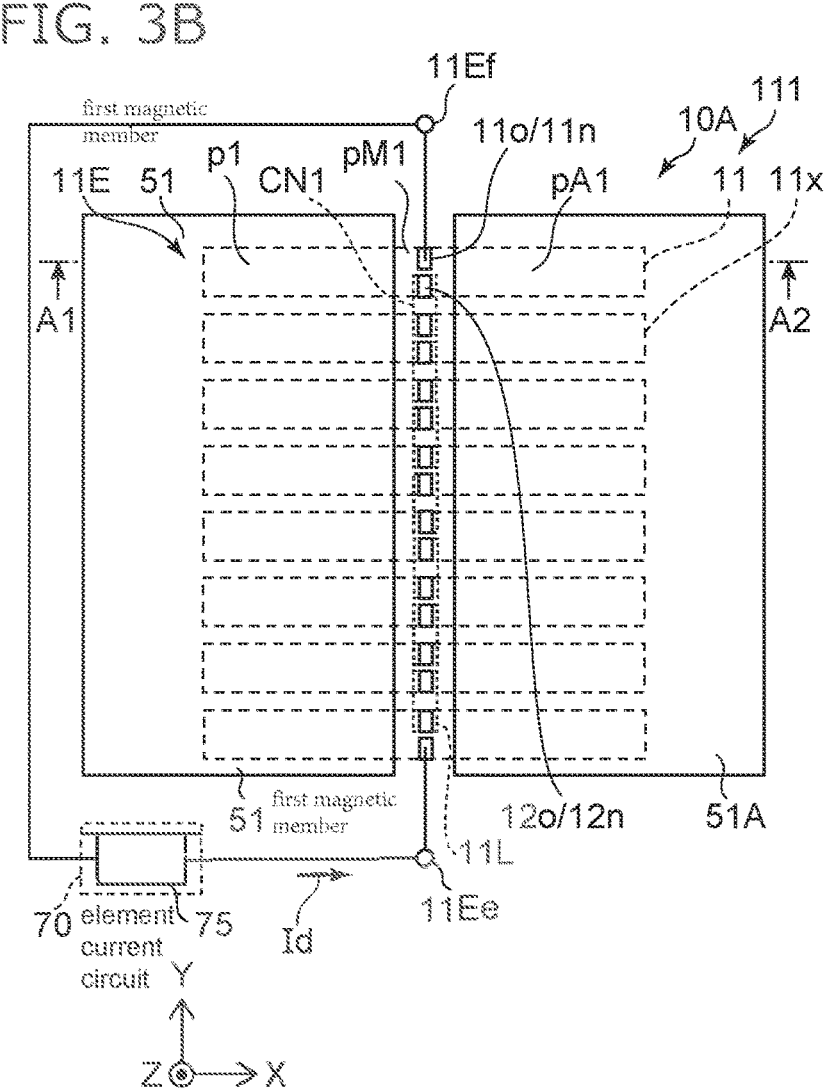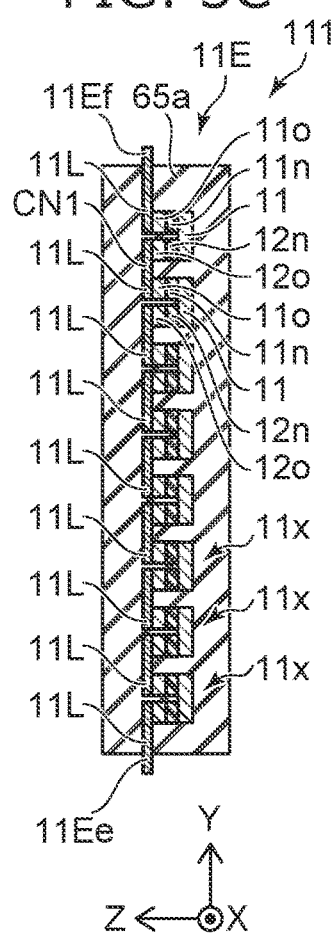

MAGNETIC SENSOR AND INSPECTION DEVICE

CROSS-REFERENCE TO RELATED APPLICATIONS

This application is based upon and claims the benefit of priority from Japanese Patent Application No. 2021-000054, filed on Jan. 4, 2021; the entire contents of which are incorporated herein by reference.

FIELD

Embodiments described herein relate generally to a magnetic sensor and an inspection device.

BACKGROUND

There is a magnetic sensor that uses a magnetic layer. There is an inspection device that uses the magnetic sensor. It is desirable to increase the sensitivity of the magnetic sensor.

BRIEF DESCRIPTION OF THE DRAWINGS

FIGS. 1A to 1C are schematic views illustrating a magnetic sensor according to a first embodiment;

FIGS. 3A to 3C are schematic views illustrating a magnetic sensor according to the first embodiment;

DETAILED DESCRIPTION

Figure 2:
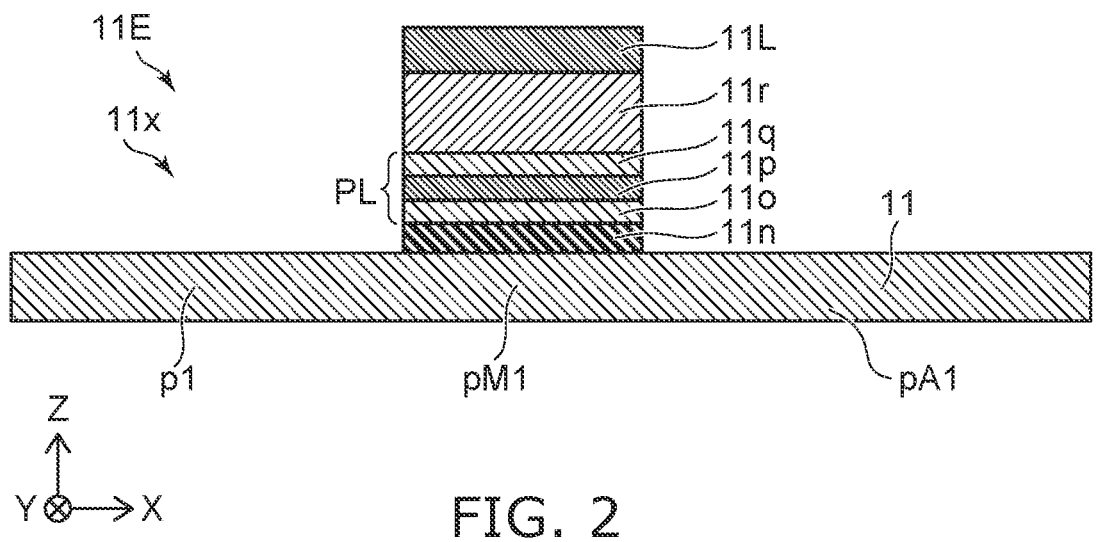
FIG. 2 is a schematic cross-sectional view illustrating a portion of the magnetic sensor according to the first embodiment.

According to one embodiment, a magnetic sensor includes a first sensor part. The first sensor part includes a first magnetic member, a first counter magnetic member, and a first magnetic element. A direction from the first magnetic member toward the first counter magnetic member is along a first direction. The first magnetic element includes one or a plurality of first extension parts. The first extension part includes a first magnetic layer, a first counter magnetic layer, and a first nonmagnetic layer. The first magnetic layer includes a first portion, a first counter portion, and a first middle portion. A direction from the first portion toward the first counter portion is along the first direction. The first middle portion is between the first portion and the first counter portion. The first nonmagnetic layer is between the first counter magnetic layer and at least a portion of the first middle portion in a second direction crossing the first direction.

According to one embodiment, an inspection device includes the magnetic sensor described above, and a processor configured to process a signal output from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIGS. 1A to 1C are schematic views illustrating a magnetic sensor according to a first embodiment. FIG. 1A is a line A1-A2 cross-sectional view of FIG. 13. FIG. 13 is a plan view. FIG. 1C is a cross-sectional view.

As shown in FIGS. 1A and 1B, the magnetic sensor 110 according to the embodiment includes a first sensor part 10A The first sensor part 10A includes a first magnetic member 51, a first counter magnetic member 51A, and a first magnetic element 11E.

The direction from the first magnetic member 51 toward the first counter magnetic member 51A is along a first direction. The first direction is taken as an X-axis direction. One direction perpendicular to the X-axis direction is taken as a Z-axis direction. A direction perpendicular to the Z-axis direction and the X-axis direction is taken as a Y-axis direction.

The first magnetic element 11E includes one or multiple first extension parts 11x. In the example, the number of the first extension parts 11x is 1, As shown in FIGS. 1A and 1C, the first extension part 11x includes a first magnetic layer 11, a first counter magnetic layer 11o, and a first nonmagnetic layer 11n.

As shown in FIGS. 1A and 1B, the first magnetic layer 11 includes a first portion p1, a first counter portion pA1, and a first middle portion pM1.

The direction from the first portion p1 toward the first counter portion pA1 is along the first direction (the X-axis direction). The first middle portion pM1 is between the first portion p1 and the first counter portion pA1. The first nonmagnetic layer 11n is between the first counter magnetic layer 11o and at least a portion of the first middle portion pM1 in a second direction. The second direction crosses the first direction. The second direction is, for example, the Z-axis direction. The direction from the first portion p1 toward the first magnetic member 51 is along the second direction. The direction from the first counter portion pA1 toward the first counter magnetic member 51A is along the second direction.

As shown in FIG. 1A, the first sensor part 10A may further include a first insulating member 65a. At least a portion of the first insulating member 65a is between the first portion p1 and the first magnetic member 51 and between the first counter portion pA1 and the first counter magnetic member 51A. The first insulating member 65a may be located around the first magnetic element 11E, the first magnetic member 51, and the first counter magnetic member 51A. The first insulating member 65a is not illustrated in FIG. 1B.

As shown in FIG. 1A, for example, the position in the first direction (the X-axis direction) of the first nonmagnetic layer 11n is between the position in the first direction of the first magnetic member 51 and the position in the first direction of the first counter magnetic member 51A. In the second direction (the Z-axis direction), the first nonmagnetic layer 11n overlaps a region 66a between the first magnetic member 51 and the first counter magnetic member 51A. The region 66a may be, a portion of the first insulating member 65a.

The first middle portion pM1, the first nonmagnetic layer 11n, and the first counter magnetic layer 11o of the first magnetic layer 11 are used as, for example, a detecting part. The electrical resistance of the detecting part changes according to a magnetic field of a detection object. The detecting part is, for example, a MTJ (Magnetic Tunnel Junction) element.

According to the embodiment, a magnetic field (the external magnetic field of the detection object) is concentrated by the first magnetic member 51 and the first counter magnetic member 51A. The concentrated magnetic field can be efficiently applied to the detecting part (e.g., the MTJ element). For example, the first magnetic member 51 and the first counter magnetic member 51A function as a MFC (Magnetic Field Concentrator).

According to the embodiment, the first portion p1 of the first magnetic layer 11 overlaps the first magnetic member 51 in the Z-axis direction. The first counter portion pA1 of the first magnetic layer 11 overlaps the first counter magnetic member 51A in the Z-axis direction. Thereby, the concentrated magnetic field (external magnetic field) is efficiently applied to the first portion p1 and the first counter portion pA1. The concentrated magnetic field is more effectively applied to the detecting part. High sensitivity is obtained thereby. According to the embodiment, for example, a magnetic sensor can be provided in which the sensitivity can be increased.

For example, the external magnetic field includes a component along the X-axis direction. The orientation of the magnetization of the first magnetic layer 11 is changed by the external magnetic field. For example, when the external magnetic field is 0, the angle between the magnetization of the first magnetic layer 11 and the magnetization of the first counter magnetic layer 11o is substantially 0. At this time, for example, these magnetizations are along the Y-axis direction. The electrical resistance of the detecting part at this time is low. On the other hand, the angle between the magnetization of the first magnetic layer 11 and the magnetization of the first counter magnetic layer 11o increases when the external magnetic field is not 0. The electrical resistance at this time is high.

A first conductive layer 11L may be provided as shown in FIG. 1A. The first counter magnetic layer 11o is located between the first middle portion pM1 and the first conductive layer 11L. The first conductive layer 11L is electrically connected with the first counter magnetic layer 11o.

In the example as shown in FIG. 1B, the first extension part 11x includes a second counter magnetic layer 12o and a second nonmagnetic layer 12n. In the example, the first nonmagnetic layer 11n is between the first counter magnetic layer 11o and a portion of the first middle portion pM1 in the second direction (the Z-axis direction). The second nonmagnetic layer 12n is between the second counter magnetic layer 12o and another portion of the first middle portion pM1 in the second direction. The direction from the second nonmagnetic layer 12n toward the first nonmagnetic layer 11n is along a third direction. The third direction crosses a plane (the Z-X plane) including the first and second directions. The third direction is, for example, the Y-axis direction. The second counter magnetic layer 12o, the second nonmagnetic layer 12n, and the other portion of the first middle portion pM1 are one detecting part (e.g., the MTJ element).

Another first conductive layer 11L that is electrically connected with the second counter magnetic layer 12o also may be provided.

The electrical resistance of the first magnetic element 11E corresponds to the electrical resistance of a current path that includes the first counter magnetic layer 11o, the first nonmagnetic layer 11n, the first magnetic layer 11, the second nonmagnetic layer 12n, and the second counter magnetic layer 12o. The electrical resistance of the first magnetic element 11E corresponds to the electrical resistance between the first conductive layer 11L electrically connected with the first counter magnetic layer 11o and the other first conductive layer 11L electrically connected with the second counter magnetic layer 12o.

As shown in FIG. 1C, for example, one end 11Ee of the first magnetic element 11E corresponds to the other first conductive layer 11L described above. For example, another end 11Ef of the first magnetic element 11E corresponds to the first conductive layer 11L described above.

As shown in FIG. 1B, the magnetic sensor 110 may include an element current circuit 75. The element current circuit 75 is configured to supply an element current Id to the first magnetic element 11E. For example, the element current circuit 75 is electrically connected with the one end 11Ee of the first magnetic element 11E and the other end 11Ef of the first magnetic element 11E. For example, the element current circuit 75 supplies the element current Id to a current path between the one end 11Ee of the first magnetic element 11E and the other end 11Ef of the first magnetic element 11E. The electrical resistance of the first magnetic element 11E can be detected using the element current Id. The element current circuit 75 may be included in a controller 70.

As shown in FIG. 1A, the length along the first direction (the X-axis direction) of the first magnetic layer 11 is taken as a first magnetic layer length L11. The distance along the first direction between the first magnetic member 51 and the first counter magnetic member 51A is taken as a first distance g1. For example, it is favorable for the first magnetic layer length L11 to be not less than 2 times the first distance g1. Thereby, as described below, the magnetic field of the detection object is more efficiently applied to the detecting part. Higher sensitivity is obtained.

The length along the first direction (the X-axis direction) of the first nonmagnetic layer 11n is taken as a first nonmagnetic layer length L11n. It is favorable for the first nonmagnetic layer length L11n to be, for example, not more than the first distance g1. Higher sensitivity is easily obtained thereby.

The length along the first direction (the X-axis direction) of the first portion p1 is taken as a first portion length Lp1. The first portion length Lp1 corresponds to the length of a region that overlaps the first magnetic member 51 of the first magnetic layer 11. In one example, it is favorable for the first portion length Lp1 to be greater than the first distance g1. High sensitivity is easily obtained. The length along the first direction (the X-axis direction) of the first counter portion pA1 is taken as a first counter portion length LpA1. The first counter portion length LpA1 corresponds to the length of a region that overlaps the first counter magnetic member 51A of the first magnetic layer 11. In one example, it is favorable for the first counter portion length LpA1 to be greater than the first distance g1. High sensitivity is easily obtained.

As shown in FIG. 1A, the distance along the second direction (the Z-axis direction) between the first portion p1 and the first magnetic member 51 is taken as a distance d1. It is favorable for the distance d1 to be, for example, less than the first distance g1. It is favorable for the distance d1 to be, for example, not more than the length (the first portion length Lp1) along the first direction (the X-axis direction) of the first portion p1. Higher sensitivity is easily obtained.

It is favorable for the distance d1 to be, for example, not less than 2 nm. The electrical insulation between the first magnetic layer 11 and the first magnetic member 51 is made more reliable thereby. The electrical insulation between the first magnetic layer 11 and the first counter magnetic member 51A becomes more reliable. The distance d1 may be, for example, not less than 10 nm.

FIG. 2 is a schematic cross-sectional view illustrating a portion of the magnetic sensor according to the first embodiment.

The first extension part 11x may further include a first layer 11r. The first layer 11r includes at least one selected from the group consisting of IrMn and PtMn. The first layer 11r is, for example, an antiferromagnetic layer. The first counter magnetic layer 11o is located between the first magnetic layer 11 (the first middle portion pM1) and the first layer 11r.

In the example, the first extension part 11x includes a magnetic film 11q and a nonmagnetic film 11p. The magnetic film 11q is between the first counter magnetic layer 11o and the first layer 11r. The nonmagnetic film 11p is between the first counter magnetic layer 11o and the magnetic film 11q. The nonmagnetic film 11p includes, for example, Ru. A layer PL that includes the first counter magnetic layer 11o, the nonmagnetic film 11p, and the magnetic film 11q functions as a reference layer. The layer PL is, for example, a fixed magnetic layer. The magnetization of the first magnetic layer 11 easily changes. The first magnetic layer 11 is, for example, a free magnetic layer.

The first nonmagnetic layer 11n includes, for example, MgO. A high MR ratio is obtained. The first magnetic layer 11, the first counter magnetic layer 11o, and the magnetic film 11q include, for example, at least one selected from the group consisting of Fe, Co, and Ni. The first magnetic layer 11, the first counter magnetic layer 11o, and the magnetic film 11q are, for example, ferromagnetic layers. The first magnetic member 51 and the first counter magnetic member 51A include, for example, at least one selected from the group consisting of NiFe and FeAlSi. The first magnetic member 51 and the first counter magnetic member 51A are, for example, soft magnetic materials. The relative magnetic permeabilities of the first magnetic member 51 and the first counter magnetic member 5A are, for example, not less than 1000.

FIGS. 3A to 3C are schematic views illustrating a magnetic sensor according to the first embodiment. FIG. 3A is a line A1-A2 cross-sectional view of FIG. 36. FIG. 3B is a plan view. FIG. 3C is a cross-sectional view.

As shown in FIGS. 3A and 3B, in the magnetic sensor 111 according to the embodiment as well, the first sensor part 10A includes the first magnetic member 51, the first counter magnetic member 51A, and the first magnetic element 11E. In the magnetic sensor 111 as shown in FIG. 3B, the first magnetic element 11E includes the multiple first extension parts 11x.

The multiple first extension parts 11x are arranged in the third direction. The third direction crosses a plane (the X-Z plane) including the first and second directions. The third direction is, for example, the Y-axis direction.

As shown in FIG. 3C, the direction from the first nonmagnetic layer 11n of one of the multiple first extension parts 11x toward the first nonmagnetic layer 11n of another one of the multiple first extension parts 11x is along the third direction (the Y-axis direction).

As shown in FIGS. 3B and 3C, the first magnetic element 11E may further include a first connection member CN1. For example, one first conductive layer 11L may be used as the first connection member CN1. The first connection member CN1 electrically connects the second counter magnetic layer 12o of one of the multiple first extension parts 11x and the first counter magnetic layer 11o of another one of the multiple first extension parts 11x.

For example, the detecting parts that are included in the multiple first extension parts 11x are electrically connected in series. For example, noise is suppressed. For example, an electrical resistance that is suited to the detection is obtained. Higher sensitivity is easily obtained.

Examples of characteristics of the magnetic sensor will now be described.

Figure 4:
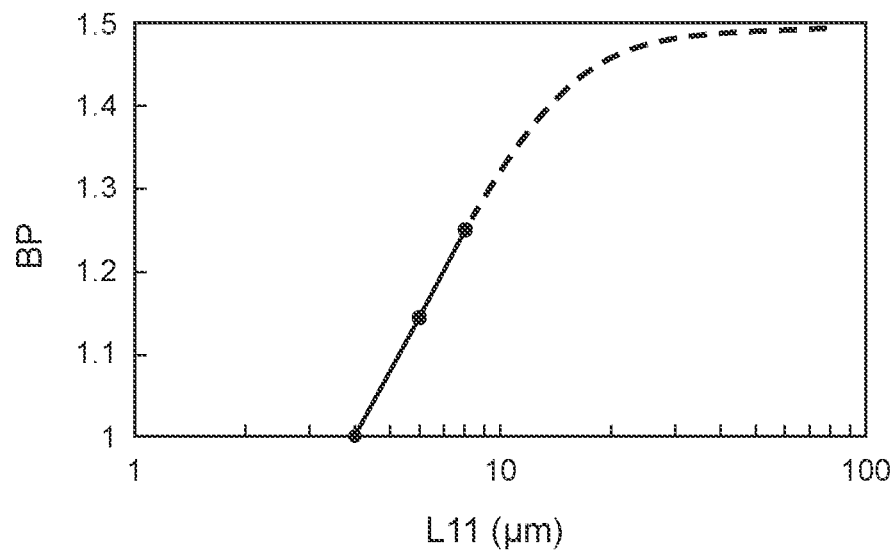
FIG. 4 is a graph illustrating a characteristic of the magnetic sensor.

FIG. 4 is a graph illustrating a characteristic of the magnetic sensor.

FIG. 4 illustrates simulation results of a characteristic when the length (the first magnetic layer length L11) along the X-axis direction of the first magnetic layer 11 is changed. In the model of the simulation, the distance (the first distance g1) between the first magnetic member 51 and the first counter magnetic member 51A is 5 μm. The length (the first nonmagnetic layer length L11n) along the X-axis direction of the first nonmagnetic layer 11n is 4 μm. When the first magnetic layer length L11 is 4 μm, the length of the first magnetic layer 11 is equal to the length of the first nonmagnetic layer 11n. The first magnetic layer length L11 is modified in such a model. In this model, the region that includes the interface between the first nonmagnetic layer 11n and the first magnetic layer 11 corresponds to a sensitive part. The length of the first magnetic layer 11 may be increased or reduced without changing the length of the sensitive part.

The horizontal axis of FIG. 4 is the first magnetic layer length L11. The vertical axis is an average magnetic flux density BP at the position of the interface between the first middle portion pIII and the first nonmagnetic layer 11n. The magnetic flux density BP is normalized to have a value of 1 when the first magnetic layer length L11 is 4 μm. The magnetic flux density BP corresponds to the sensitivity of the detection of the external magnetic field.

As shown in FIG. 4, the magnetic flux density BP increases as the first magnetic layer length L11 increases.

According to the embodiment, for example, it is favorable for the first magnetic layer length L11 to be not less than 2 times the first distance g1. Thereby, the magnetic field of the detection object is the more efficiently applied to the detecting part. Higher sensitivity is obtained.

Figure 5:
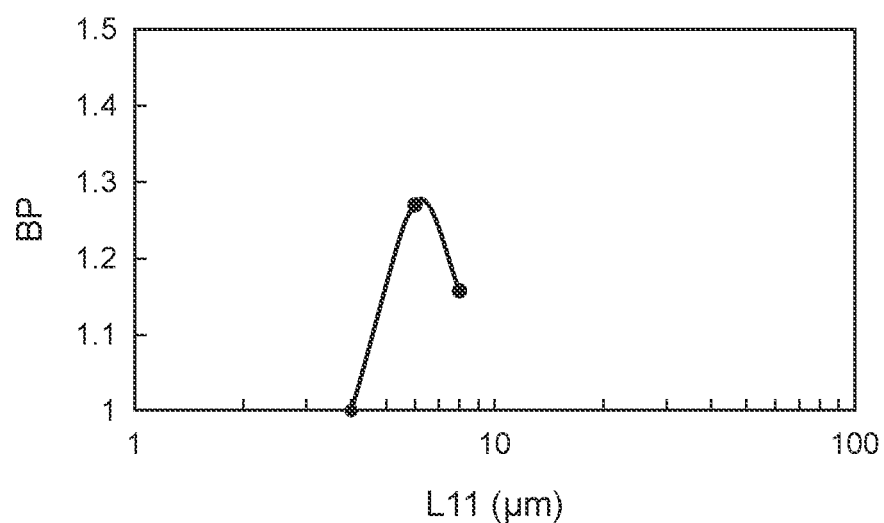
FIG. 5 is a graph illustrating a characteristic of the magnetic sensor.

FIG. 5 is a graph illustrating a characteristic of the magnetic sensor.

In the model of the simulation of FIG. 5, the lengths in the X-axis direction of the first nonmagnetic layer 11n and the first counter magnetic layer 11o are equal to the length (the first magnetic layer length L11) in the X-axis direction of the first magnetic layer 11. The lengths in the X-axis direction of the first nonmagnetic layer 11n and the first counter magnetic layer 11o change conjunctively with the change of the first magnetic layer length L11. In the model of the simulation, the first distance g1 is 5 μm. In the model of FIG. 5 as well, a region that includes the interface between the first nonmagnetic layer 11n and the first magnetic layer 11 corresponds to the sensitive part. In the model of FIG. 5, the length of the sensitive part changes conjunctively according to the change of the first magnetic layer length L11.

The horizontal axis of FIG. 5 is the first magnetic layer length L11. The vertical axis is the average magnetic flux density BP at the position of the interface between the first middle portion pM1 and the first nonmagnetic layer 11n. The magnetic flux density BP is normalized to have a value of 1 when the first magnetic layer length L11 is 4 μm.

In this model as shown in FIG. 5, the magnetic flux density BP decreases when the first magnetic layer length L11 becomes excessively long. This is caused by the length of the sensitive part increasing conjunctively with the increase of the first magnetic layer length L11.

As described above, it is favorable to maintain a short length in the X-axis direction of the first nonmagnetic layer 11n and for the length in the X-axis direction of the first magnetic layer 11 to be long. A high magnetic flux density BP is obtained thereby. For example, high sensitivity is obtained.

Figure 6A:
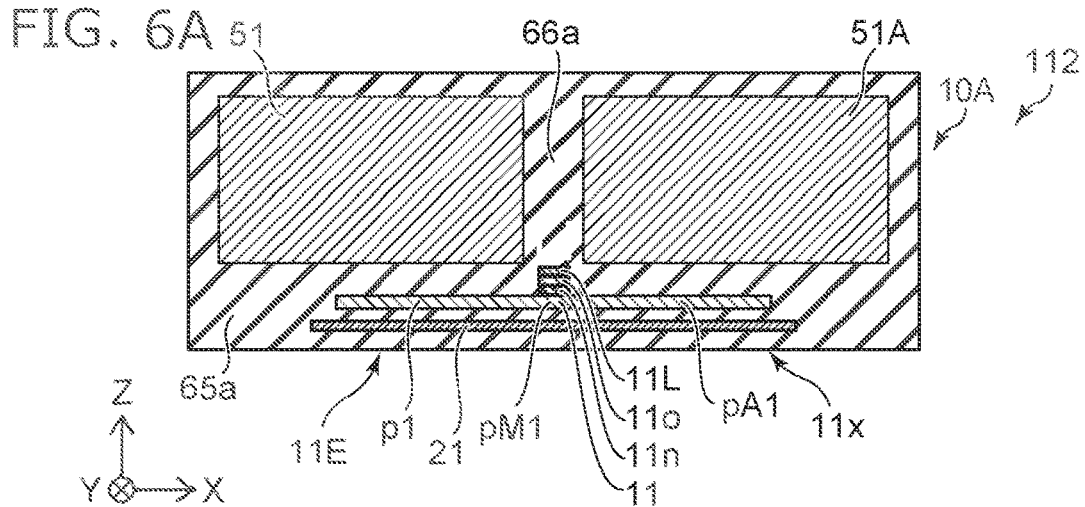
FIGS. 6A to 6C are schematic views illustrating a magnetic sensor according to the first embodiment.
Figure 6B:
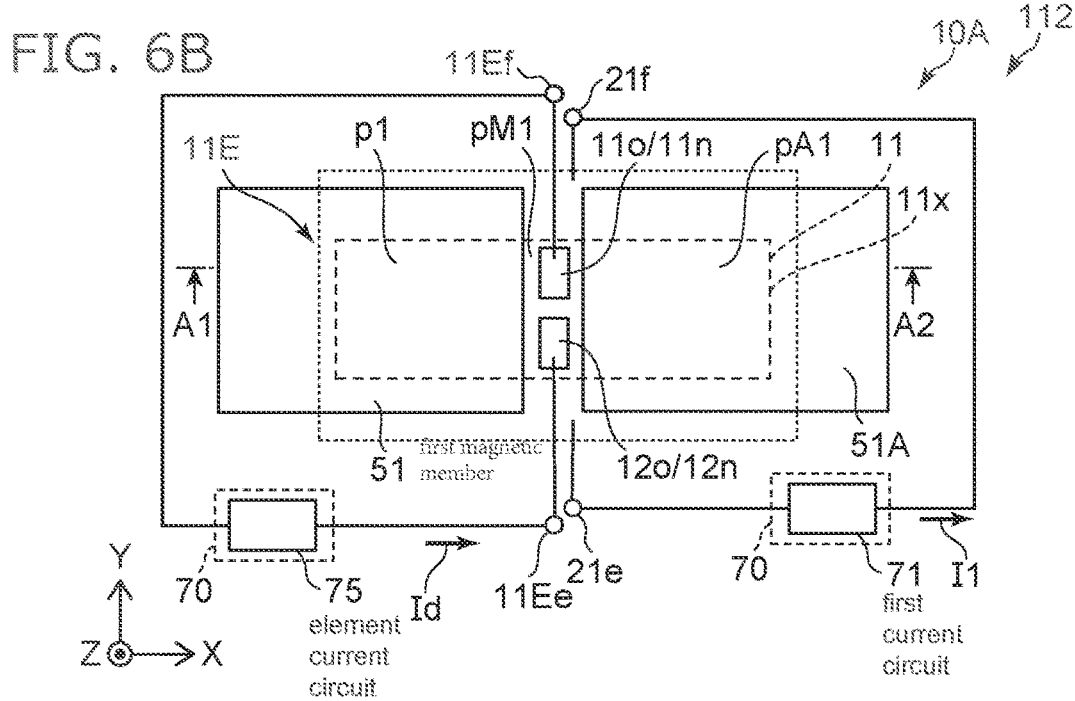
Figure 6C:
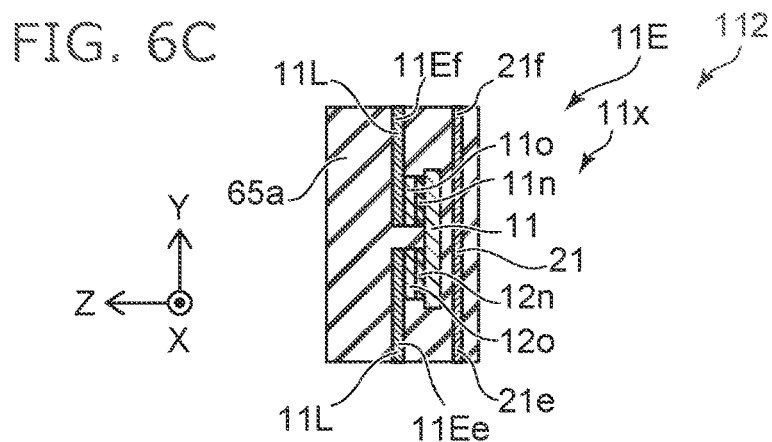

FIGS. 6A to 6C are schematic views illustrating a magnetic sensor according to the first embodiment. FIG. 6A is a line A1-A2 cross-sectional view of FIG. 6B. FIG. 6B is a plan view. FIG. 6C is a cross-sectional view.

In the magnetic sensor 112 according to the embodiment as shown in FIGS. 6A and 6B, the first sensor part 10A includes a first conductive member 21 in addition to the first magnetic member 51, the first counter magnetic member 51A, and the first magnetic element 11E. Otherwise, the configuration of the magnetic sensor 112 may be similar to the configuration of the magnetic sensor 110.

In the second direction (the Z-axis direction), at least a portion of the first conductive member 21 overlaps the region 66a between the first magnetic member 51 and the first counter magnetic member 51A. A first current I1 that includes an alternating current component can flow in the first conductive member 21. The first current I1 flows through the first conductive member 21 along the third direction. The third direction crosses a plane (the Z-X plane) including the first and second directions. The third direction is, for example, the Y-axis direction.

The magnetic sensor 112 may include a first current circuit 71. The first current circuit 71 is configured to supply the first current Z1 to the first conductive member 21. The first current circuit 71 may be included in the controller 70.

For example, the first current circuit 71 is electrically connected to one end 21e of the first conductive member 21 and another end 21f of the first conductive member 21. The first current I1 flows between the one end 21e and the other end 21f.

By the first current I1 that includes the alternating current component flowing in the first conductive member 21, a magnetic field (an alternating current magnetic field) that is based on the first current I1 is applied to the detecting part of the first magnetic element 11E. The alternating current magnetic field includes, for example, a component along the X-axis direction. The alternating current magnetic field is concentrated by the first magnetic member 51 and the first counter magnetic member 51A. The concentrated alternating current magnetic field is applied to the detecting part. The alternating current magnetic field is efficiently applied to the detecting part. As described below, unnecessary noise is suppressed by using the alternating current magnetic field. Higher sensitivity is obtained.

Figure 7A:
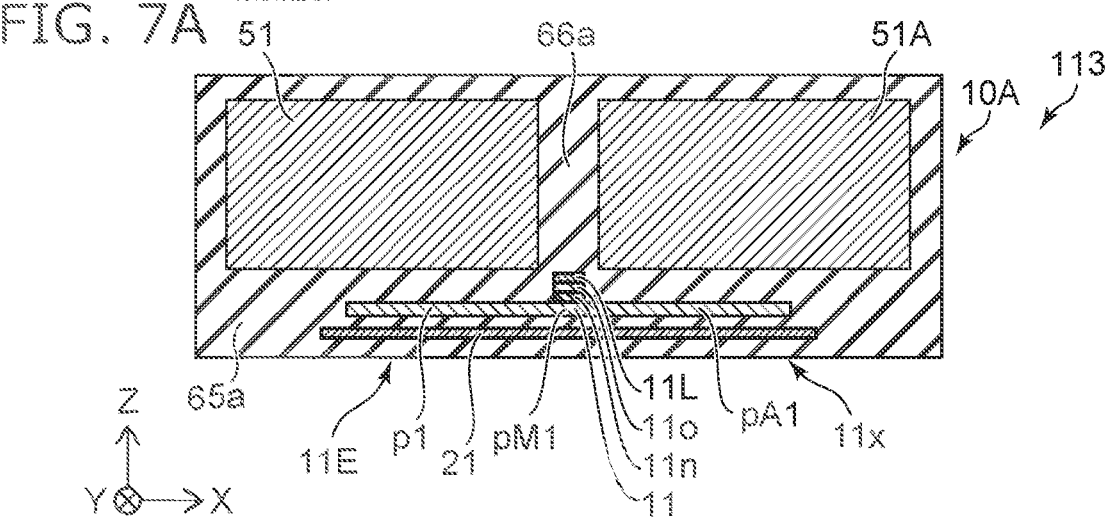
FIGS. 7A and 7B are schematic views illustrating a magnetic sensor according to the first embodiment.
Figure 7B:
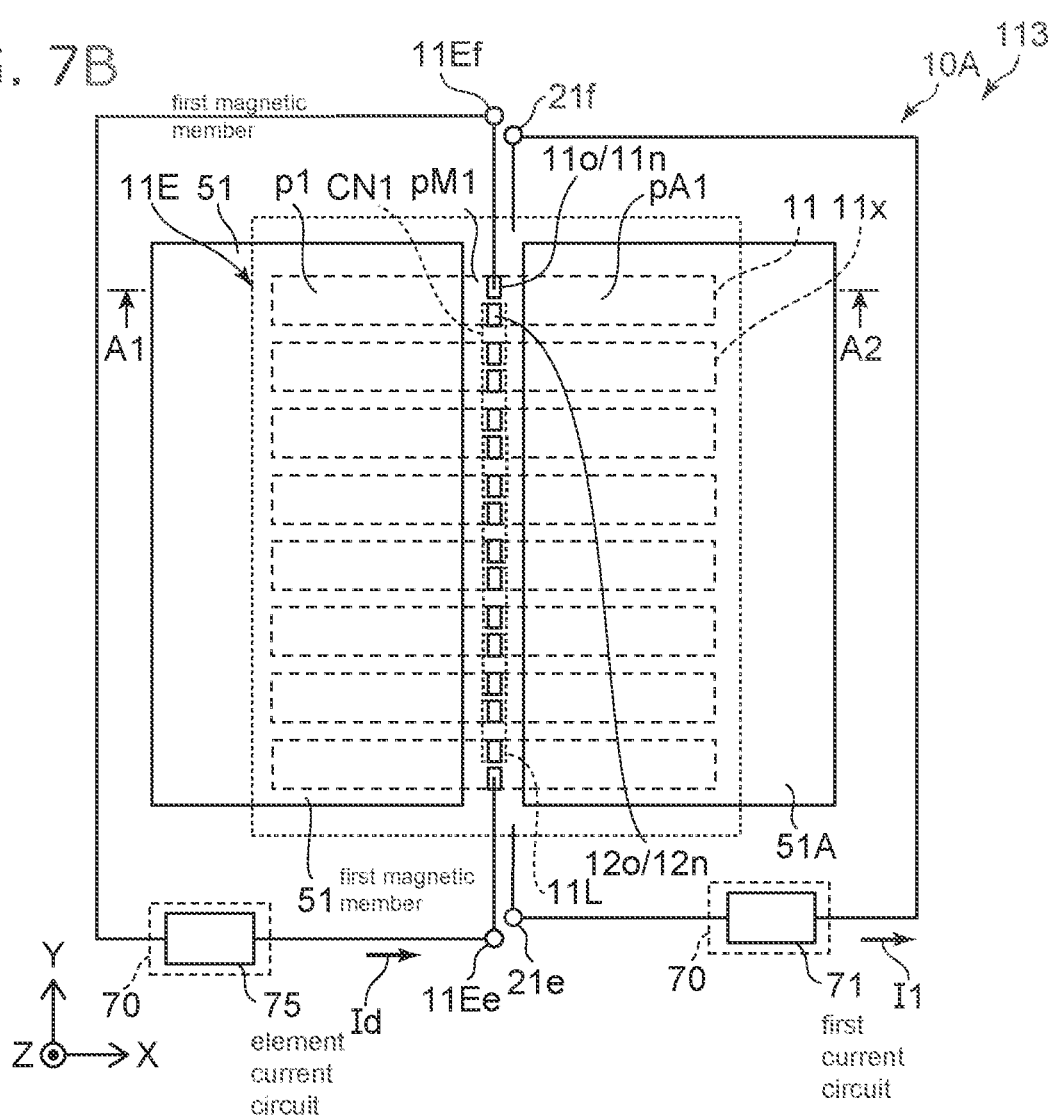

FIGS. 7A and 7B are schematic views illustrating a magnetic sensor according to the first embodiment.

FIG. 7A is a line A1-A2 cross-sectional view of FIG. 7B. FIG. 7B is a plan view.

Figure 8:
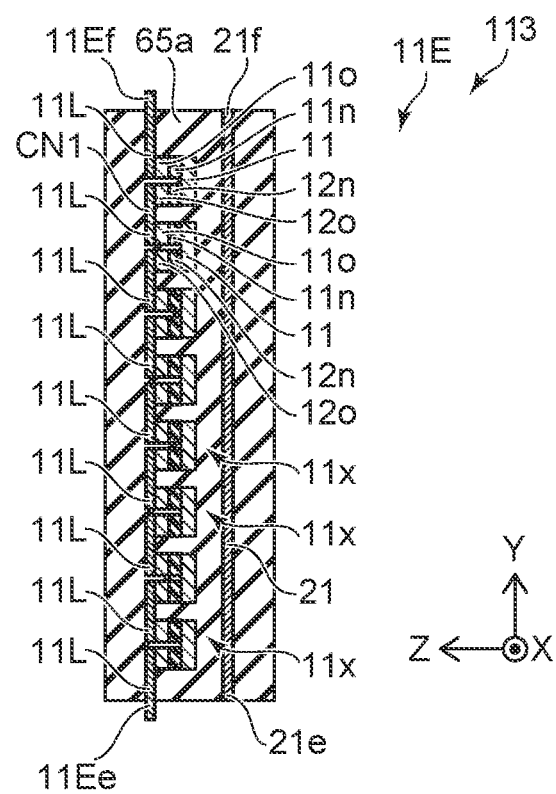
FIG. 8 is a schematic cross-sectional view illustrating the magnetic sensor according to the first embodiment.

FIG. 8 is a schematic cross-sectional view illustrating the magnetic sensor according to the first embodiment.

In the magnetic sensor 113 according to the embodiment as shown in FIGS. 7A and 7B, the first sensor part 10A includes the first conductive member 21 in addition to the first magnetic member 51, the first counter magnetic member 51A, and the first magnetic element 11E. Otherwise, the configuration of the magnetic sensor 113 may be similar to the configuration of the magnetic sensor 111. For example, the magnetic sensor 113 includes the multiple first extension parts 11x as shown in FIGS. 7A and 8.

In the magnetic sensor 113 as well, in the second direction (the Z-axis direction), at least a portion of the first conductive member 21 overlaps the region 66a between the first magnetic member 51 and the first counter magnetic member 51A. The first current I1 that includes an alternating current component can flow in the first conductive member 21 along the third direction (the Y-axis direction). The alternating current magnetic field that is based on the first current I1 is concentrated by the first magnetic member 51 and the first counter magnetic member 51A. The concentrated alternating current magnetic field is efficiently applied to the detecting part. Higher sensitivity is obtained.

In the magnetic sensor (e.g., the magnetic sensors 110 to 113, etc.) according to the first embodiment, the electrical resistance of the first magnetic element 11E has an even-function characteristic with respect to the magnetic field applied to the first magnetic element 11E. The magnetic field includes, for example, an external magnetic field of the detection object. The magnetic field may include a magnetic field (an alternating current magnetic field) based on the first current I1 including the alternating current component. For example, the electrical resistance of the first magnetic element 11E has an even-function characteristic with respect to the first current I1 supplied to the first conductive member 21. As described above, the magnetic field includes a component along the X-axis direction.

An example of the electrical resistance of the first magnetic element 11E will now be described.

Figure 9A:
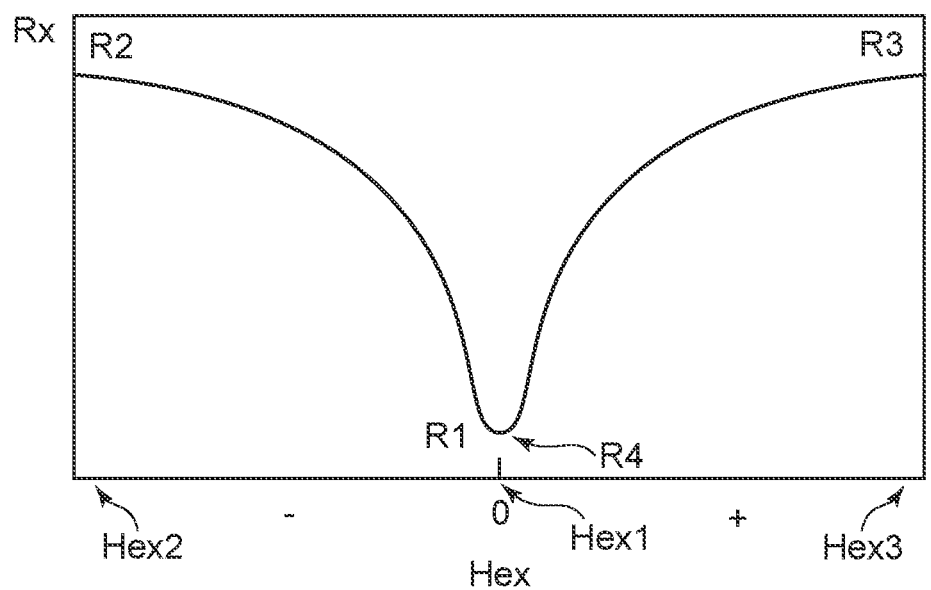
FIGS. 9A and 9B are graphs illustrating characteristics of the magnetic sensor according to the first embodiment.
Figure 9B:
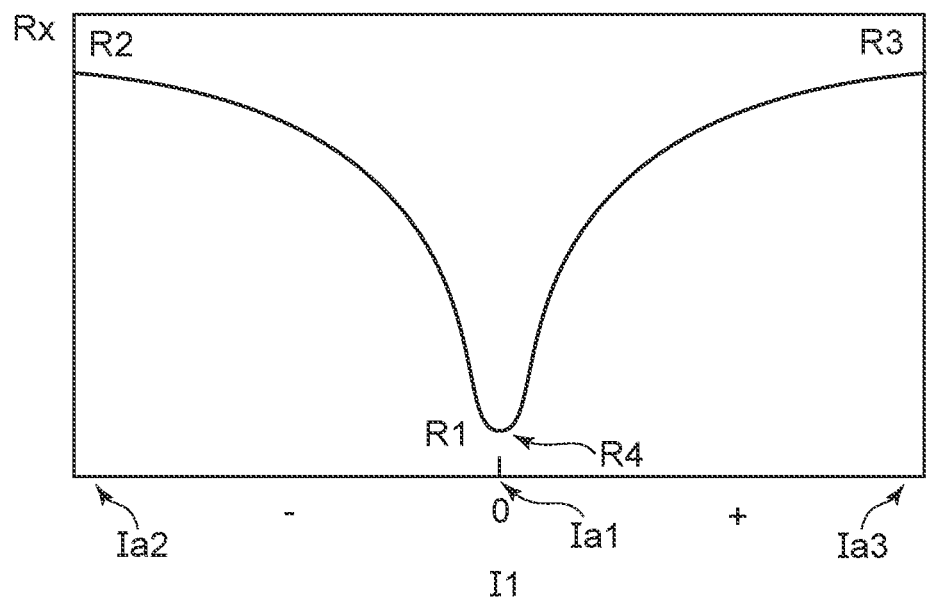

FIGS. 9A and 9B are graphs illustrating characteristics of the magnetic sensor according to the first embodiment.

The horizontal axis of FIG. 9A is the intensity of an external magnetic field Hex applied to the first magnetic element 11E. The vertical axis of FIG. 9A is an electrical resistance Rx of the first magnetic element 11E. For example, the electrical resistance Rx corresponds to the electrical resistance between the one end 11Ee of the first magnetic element 11E and the other end 11Ef of the first magnetic element 11E. FIG. 9A corresponds to an R-H characteristic. The external magnetic field Hex has an X-axis direction component.

As shown in FIG. 9A, the electrical resistance Rx has an even-function characteristic with respect to the external magnetic field Hex. For example, the electrical resistance Rx of the first magnetic element 11E has a first value R1 when a first magnetic field Hex1 is applied to the first magnetic element 11E. The electrical resistance Rx has a second value R2 when a second magnetic field Hex2 is applied to the first magnetic element 11E. The electrical resistance Rx has a third value R3 when a third magnetic field Hex3 is applied to the first magnetic element 11E. The absolute value of the first magnetic field Hex1 is less than the absolute value of the second magnetic field Hex2 and less than the absolute value of the third magnetic field Hex3. The orientation of the second magnetic field Hex2 is opposite to the orientation of the third magnetic field Hex3. The first value R1 is less than the second value R2 and less than the third value R3.

For example, the first magnetic field Hex1 is substantially 0. The electrical resistance Rx has a fourth value R4 when the external magnetic field Hex is not applied to the first magnetic element 11E. The first value R1 may be substantially equal to the fourth value R4 when the external magnetic field Hex is not applied. For example, the ratio of the absolute value of the difference between the first value R1 and the fourth value R4 to the fourth value R4 is not more than 0.01. The ratio may be not more than 0.001. A substantially even-function characteristic is obtained for the positive and negative external magnetic fields.

The horizontal axis of FIG. 9B is the first current I1 that is supplied to the first conductive member 21. The vertical axis of FIG. 9B is the electrical resistance Rx of the first magnetic element 11E. As shown in FIG. 9B, the electrical resistance Rx has an even-function characteristic with respect to the first current I1.

For example, the electrical resistance Rx of the first magnetic element 11E has the first value R1 when a first-value current Ia1 is supplied to the first conductive member 21. The electrical resistance Rx has the second value R2 when a second-value current Ia2 is supplied to the first conductive member 21. The electrical resistance Rx has the third value R3 when a third-value current Ia3 is supplied to the first conductive member 21. The absolute value of the first-value current Ia1 is less than the absolute value of the second-value current Ia2 and less than the absolute value of the third-value current Ia3. For example, the first-value current Ia1 may be substantially 0. The orientation of the second-value current Ia2 is opposite to the orientation of the third-value current Ia3.

For example, the first-value current Ia1 is substantially 0. For example, the electrical resistance Rx is the fourth value R4 when a current does not flow to the first conductive member 21. For example, the first value R1 is substantially equal to the fourth value R4 when a current does not flow. For example, the ratio of the absolute value of the difference between the first value R1 and the fourth value R4 to the fourth value R4 is not more than 0.01. The ratio may be not more than 0.001. A substantially even-function characteristic is obtained for the positive and negative currents.

By utilizing such an even-function characteristic, highly-sensitive detection is possible as follows.

An example will now be described in which the first current I1 is an alternating current and substantially does not include a direct current component. The first current I1 (the alternating current) is supplied to the first conductive member 21; and an alternating current magnetic field due to the alternating current is applied to the first magnetic element 11E. An example of the change of the electrical resistance Rx at this time will be described.

Figure 10A:
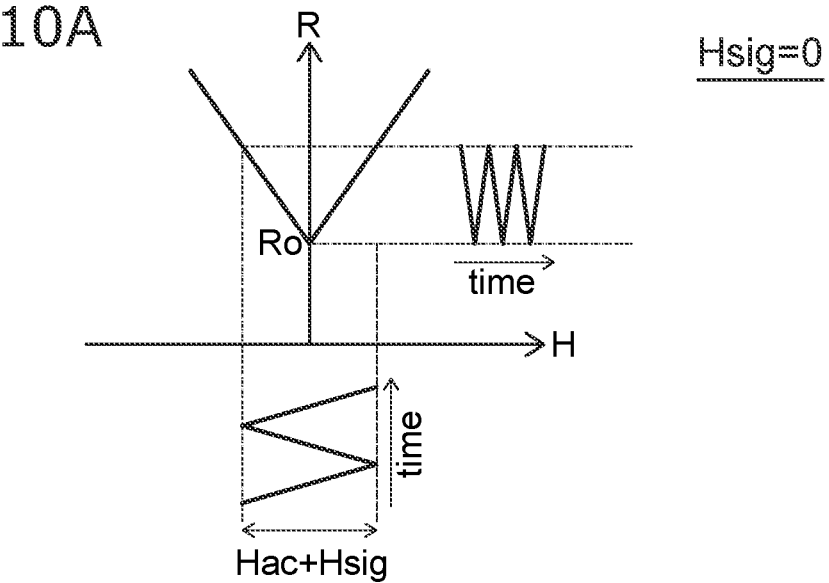
FIGS. 10A to 10C are graphs illustrating characteristics of the magnetic sensor according to the first embodiment.
Figure 10B:
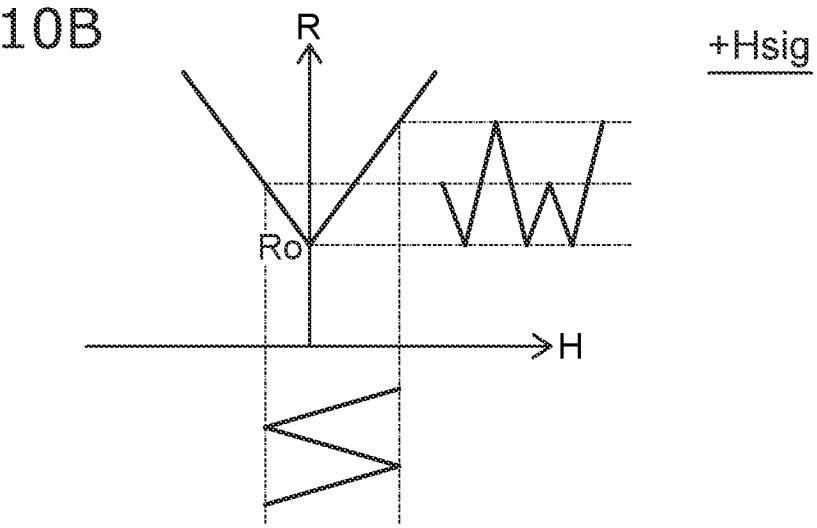
Figure 10C:
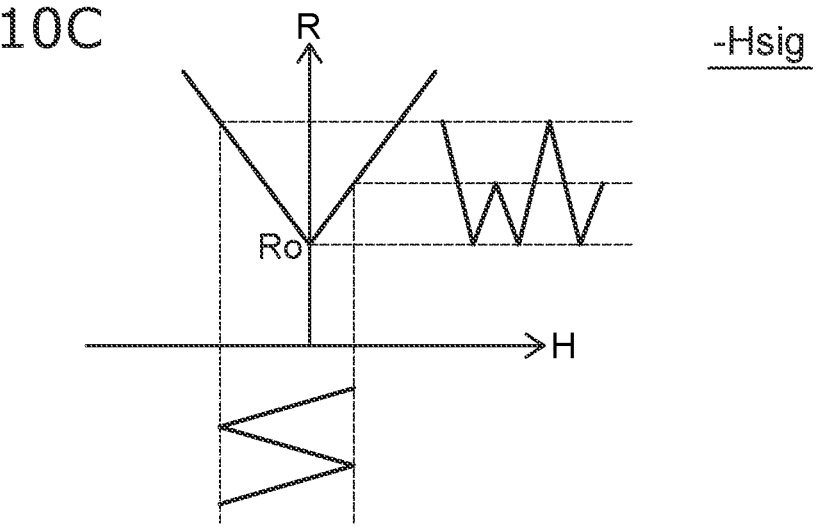

FIGS. 10A to 10C are graphs illustrating characteristics of the magnetic sensor according to the first embodiment.

FIG. 10A shows characteristics when a signal magnetic field Hsig (an external magnetic field) applied to the first magnetic element 11E is 0. FIG. 10B shows characteristics when the signal magnetic field Hsig is positive. FIG. 10C shows characteristics when the signal magnetic field Hsig is negative. These figures show the relationship between a magnetic field H and a resistance R (corresponding to the electrical resistance Rx).

As shown in FIG. 10A, when the signal magnetic field Hsig is 0, the resistance R has a characteristic that is symmetric with respect to the positive and negative magnetic field H. When an alternating current magnetic field Hac is zero, the resistance R is a low resistance Ro. For example, the magnetization of the free magnetic layer is rotated substantially identically to the positive and negative magnetic field H. Therefore, a symmetric resistance change is obtained. The change of the resistance R with respect to the alternating current magnetic field Hac has the same value between the positive and negative polarities. The period of the change of the resistance R is ½ times the period of the alternating current magnetic field Hac. The change of the resistance R substantially does not include the frequency component of the alternating current magnetic field Hac.

As shown in FIG. 10B, the characteristic of the resistance R shifts to the positive magnetic field H side when a positive signal magnetic field Hsig is applied. For example, the resistance R becomes high for the alternating current magnetic field Hac on the positive side. The resistance R becomes low for the alternating current magnetic field Hac on the negative side.

As shown in FIG. 10C, the characteristic of the resistance R shifts to the negative magnetic field H side when a negative signal magnetic field Hsig is applied. For example, the resistance R becomes low for the alternating current magnetic field Hac on the positive side. The resistance R becomes high for the alternating current magnetic field Hac on the negative side.

Change in the resistance R is different for the positive and negative of the alternating current magnetic field Hac when a signal magnetic field Hsig with non-zero magnitude is applied. The period of the change of the resistance R with respect to the positive and negative of the alternating current magnetic field Hac is equal to the period of the alternating current magnetic field Hac. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating current magnetic field Hac is taken as an alternating current frequency fac. In such a case, an output that corresponds to the signal magnetic field Hsig is generated at the frequency of fac±fsig.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, the signal magnetic field Hsig can be detected with high accuracy by extracting an output voltage having the same period (frequency) component (alternating current frequency component) as the period (the frequency) of the alternating current magnetic field Hac. In the magnetic sensor (the magnetic sensor 112 or the magnetic sensor 113) according to the embodiment, the external magnetic field Hex (the signal magnetic field Hsig) that is the detection object can be detected with high sensitivity by utilizing such characteristics According to the embodiment, the external magnetic field Hex (the signal magnetic field Hsig) and the alternating current magnetic field Hac due to the first current I1 can be efficiently applied to the first magnetic element 11E by the first magnetic member 51 and the first counter magnetic member 51A. High sensitivity is obtained.

Second Embodiment

Figure 11A:
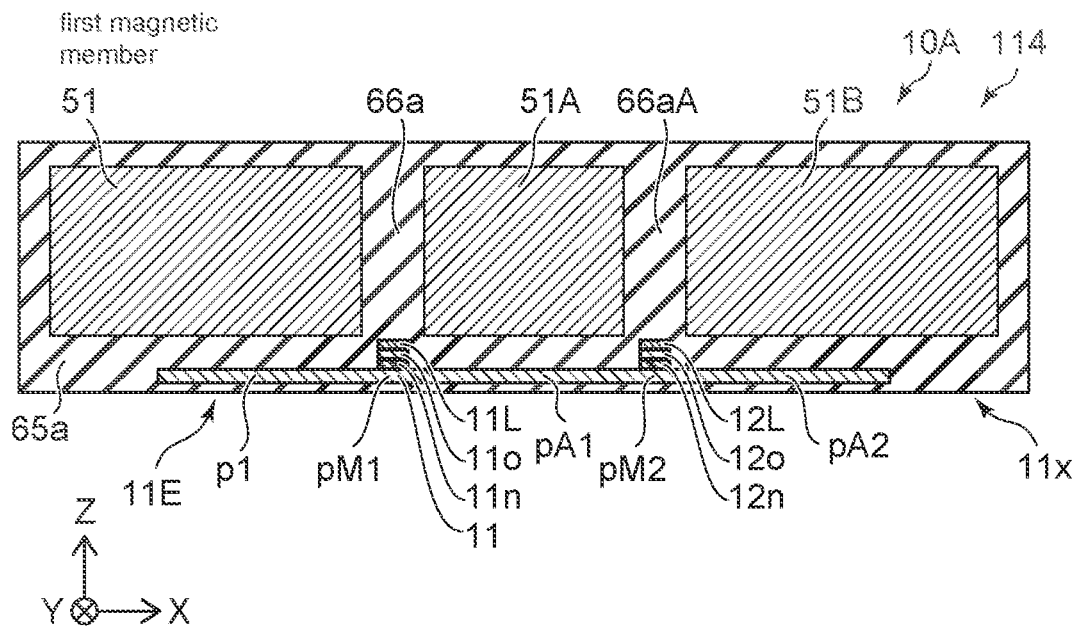
FIGS. 11A and 11B are schematic views illustrating a magnetic sensor according to a second embodiment.
Figure 11B:
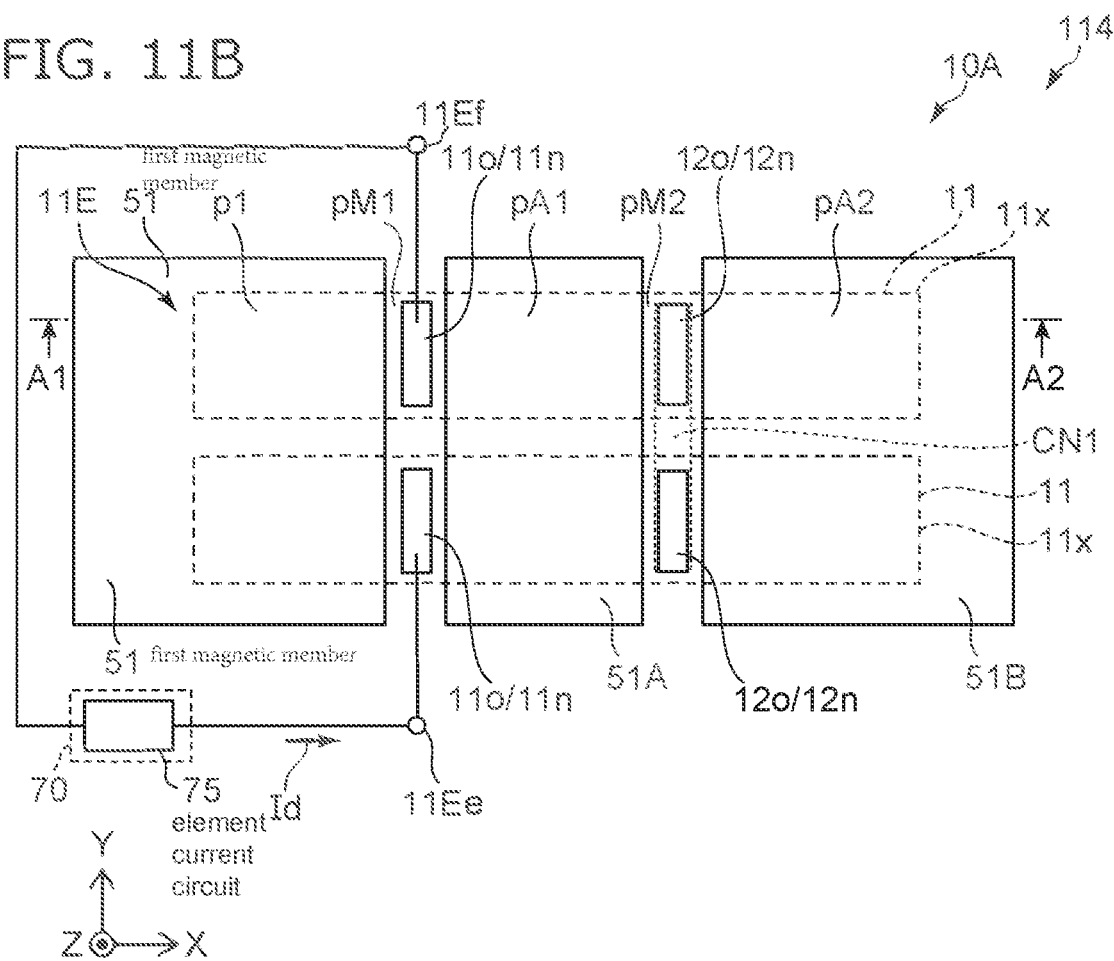

FIGS. 11A and 11B are schematic views illustrating a magnetic sensor according to a second embodiment.

FIG. 11A is a line A1-A2 cross-sectional view of FIG. 11B. FIG. 11B is a plan view.

Figure 12A:
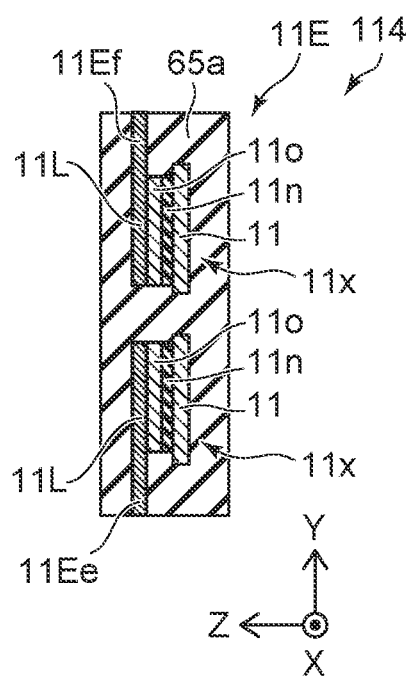
FIGS. 12A and 12B are schematic cross-sectional views illustrating the magnetic sensor according to the second embodiment.
Figure 12B:
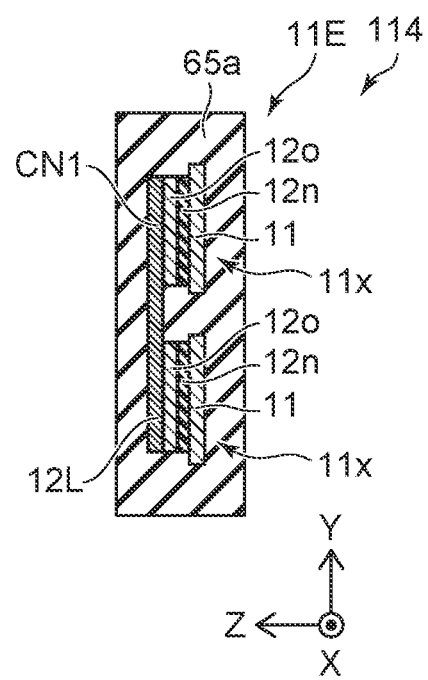

FIGS. 12A and 12B are schematic cross-sectional views illustrating the magnetic sensor according to the second embodiment.

As shown in FIGS. 11A and 11B, the magnetic sensor 114 according to the embodiment includes the first sensor part 10A. The first sensor part 10A further includes another first counter magnetic member 51B in addition to the first magnetic member 51, the first counter magnetic member 51A, and the first magnetic element 11E.

The first counter magnetic member 51A is between the first magnetic member 51 and the other first counter magnetic member 51B in the first direction (the X-axis direction).

As shown in FIG. 11A, the first extension part 11x further includes the second counter magnetic layer 12o and the second nonmagnetic layer 12n in addition to the first magnetic layer 11, the first counter magnetic layer 11o, and the first nonmagnetic layer 11n. The first magnetic layer 11 further includes a second counter portion pA2 and a second middle portion pM2 in addition to the first portion p1, the first counter portion pA1, and the first middle portion pM1. The first counter portion pA1 is between the first portion p1 and the second counter portion pA2 in the first direction (the X-axis direction). The second middle portion pM2 is between the first counter portion pA1 and the second counter portion pA2.

As shown in FIG. 11A, the first nonmagnetic layer 11n is between the first counter magnetic layer 11o and at least a portion of the first middle portion pM1 in the second direction (the Z-axis direction). As shown in FIG. 11A, the second nonmagnetic layer 12n is between the second counter magnetic layer 12o and at least a portion of the second middle portion pM2 in the second direction (the Z-axis direction).

The electrical resistance of the first magnetic element 11E corresponds to the electrical resistance of a current path that includes the first magnetic layer 11, the first counter magnetic layer 11o, the first nonmagnetic layer 11n, the second nonmagnetic layer 12n, and the second counter magnetic layer 12o.

In the example as shown in FIG. 11B, the first magnetic element 11E includes the multiple first extension parts 11x and the first connection member CN1. The multiple first extension parts 11x are arranged along the third direction. The third direction crosses a plane (the Z-X plane) including the first and second directions. The third direction is, for example, the Y-axis direction.

As shown in FIGS. 11B and 12B, the first connection member CN1 electrically connects the second counter magnetic layer 12o of one of the multiple first extension parts 11x and the second counter magnetic layer 12o of another one of the multiple first extension parts 11x.

For example, the first counter magnetic layer 11o of the other one of the multiple first extension parts 11x is the one end 11Ee of the first magnetic element 11E. The first counter magnetic layer 11o of the one of the multiple first extension parts 11x is the other end 11Ef of the first magnetic element 11E.

As shown in FIG. 11B, for example, the element current circuit 75 supplies the element current Id to a current path between the one end 11Ee of the first magnetic element 11E and the other end 11Ef of the first magnetic element 11E. A value that corresponds to the electrical resistance of the first magnetic element 11E can be detected using the change of the element current Id.

Figure 13A:
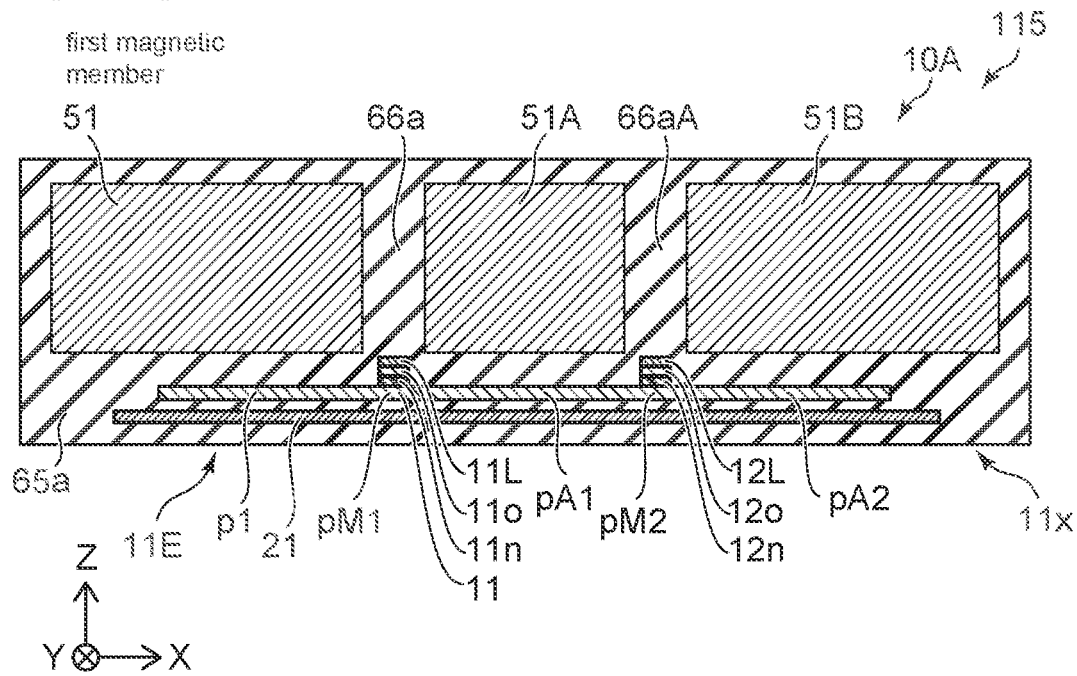
FIGS. 13A and 13B are schematic views illustrating a magnetic sensor according to the second embodiment.
Figure 13B:
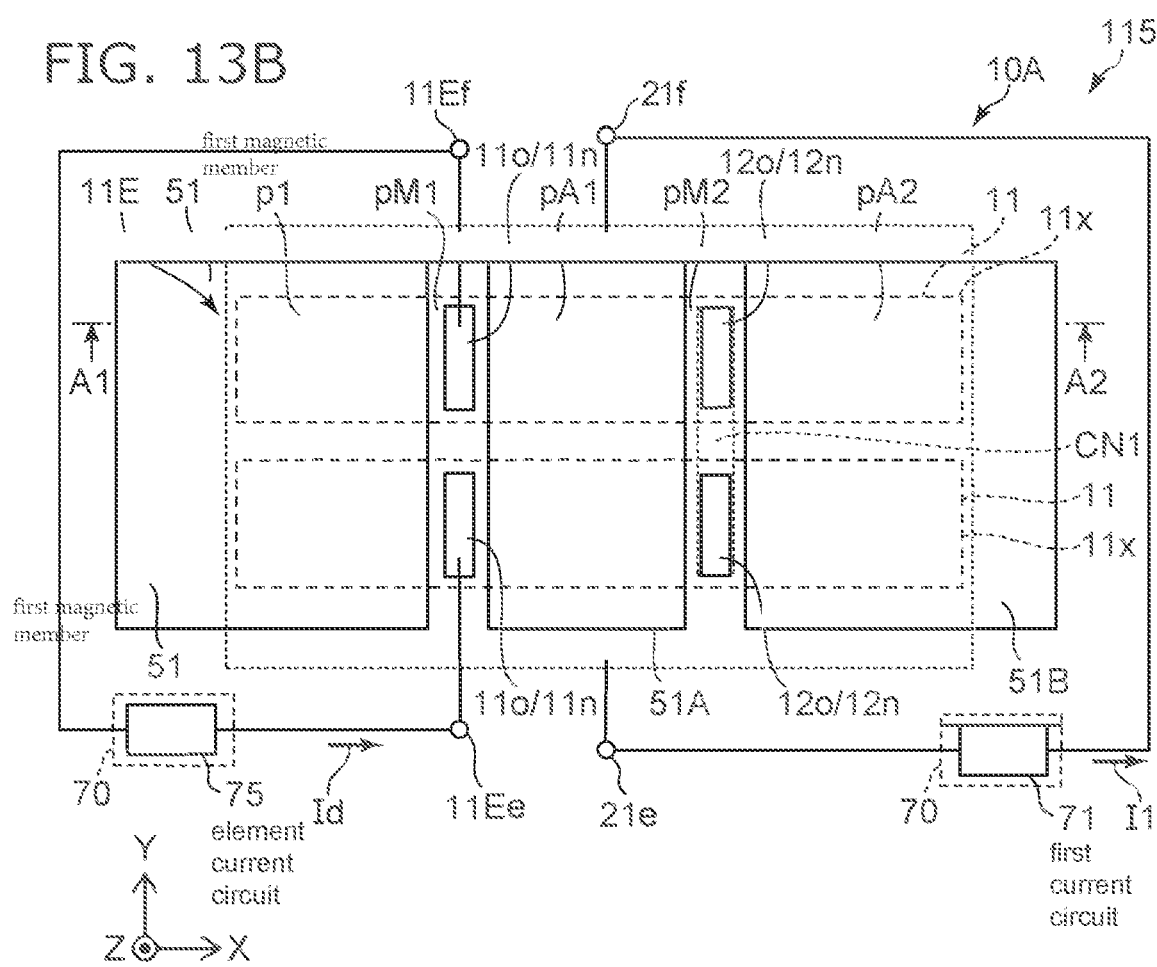

FIGS. 13A and 13B are schematic views illustrating a magnetic sensor according to the second embodiment.

FIG. 13A is a line A1-A2 cross-sectional view of FIG. 13B. FIG. 13B is a plan view.

Figure 14A:
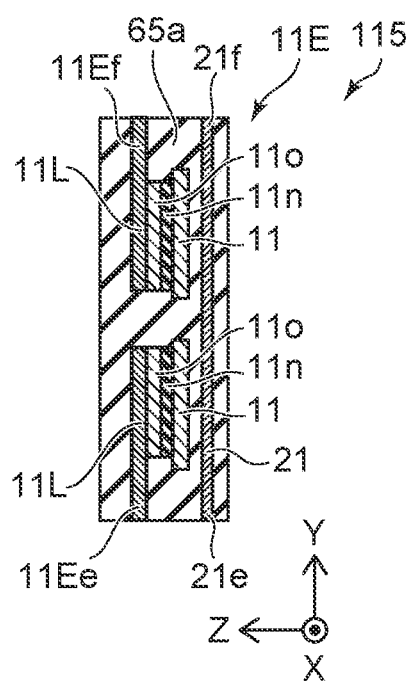
FIGS. 14A and 14B are schematic cross-sectional views illustrating the magnetic sensor according to the second embodiment.
Figure 14B:
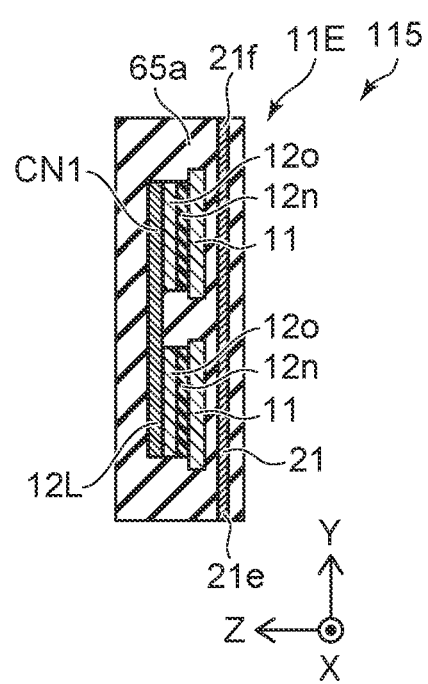

FIGS. 14A and 14B are schematic cross-sectional views illustrating the magnetic sensor according to the second embodiment.

In the magnetic sensor 115 according to the embodiment as shown in FIGS. 13A and 13B, the first sensor part 10A further includes the first conductive member 21 in addition to the first magnetic member 51, the first counter magnetic member 51A, the first magnetic element 11E, and the other first counter magnetic member 51B. Otherwise, the configuration of the magnetic sensor 115 may be similar to the configuration of the magnetic sensor 114.

In the magnetic sensor 115, in the second direction (the Z-axis direction), the first conductive member 21 overlaps the region 66a between the first magnetic member 51 and the first counter magnetic member 51A and a region 66a A between the first counter magnetic member 51A and the other first counter magnetic member 51B.

The first current circuit 71 is electrically connected with the one end 21e of the first conductive member 21 and the other end 21f of the first conductive member 21. The first current that includes an alternating current component is supplied from the first current circuit 71 to the first conductive member 21.

Third Embodiment

FIG. 15, FIG. 16, and FIGS. 17A to 17C are schematic views illustrating a magnetic sensor according to a third embodiment.

Figure 15:
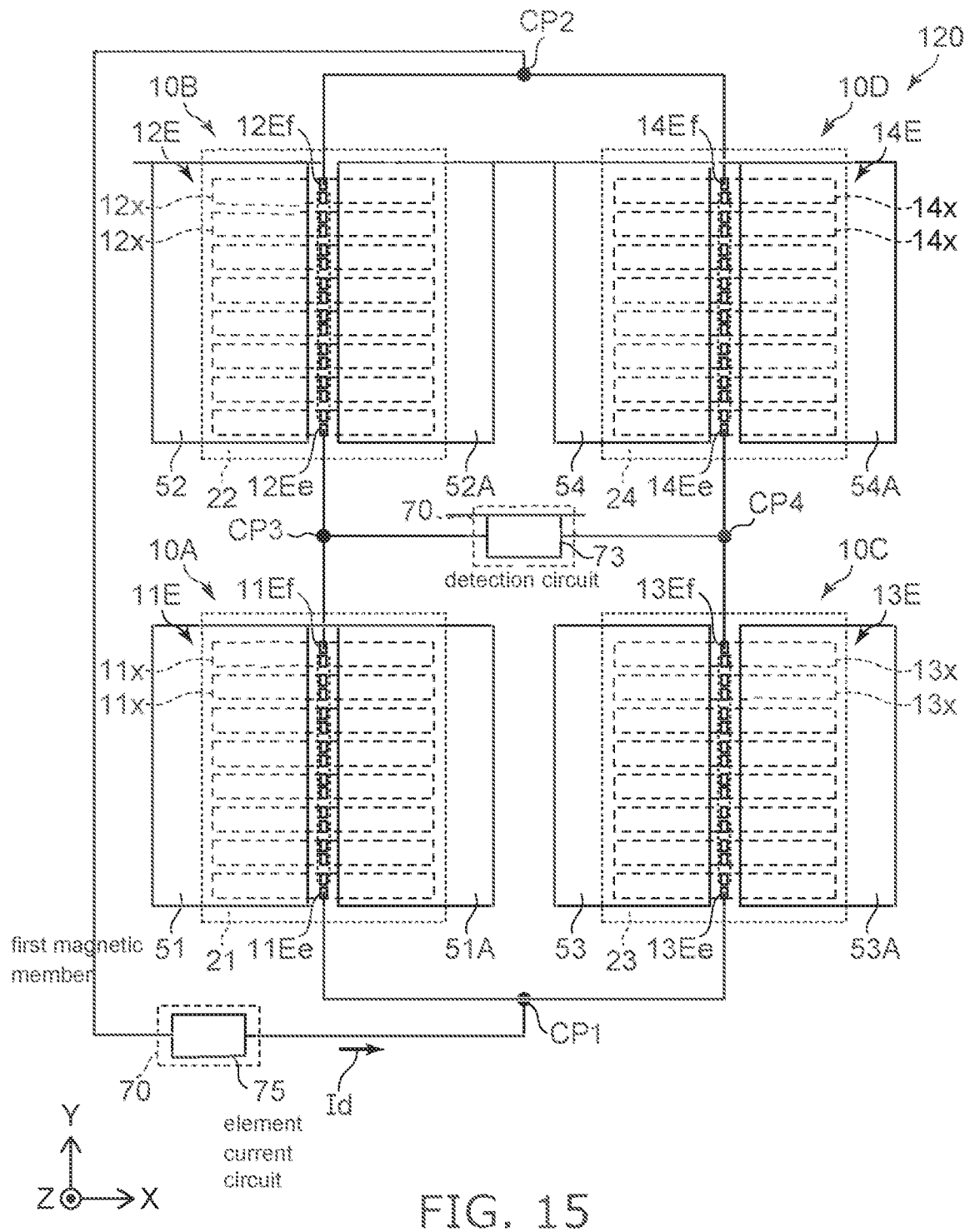
FIG. 15 is a schematic view illustrating a magnetic sensor according to a third embodiment.
Figure 16:
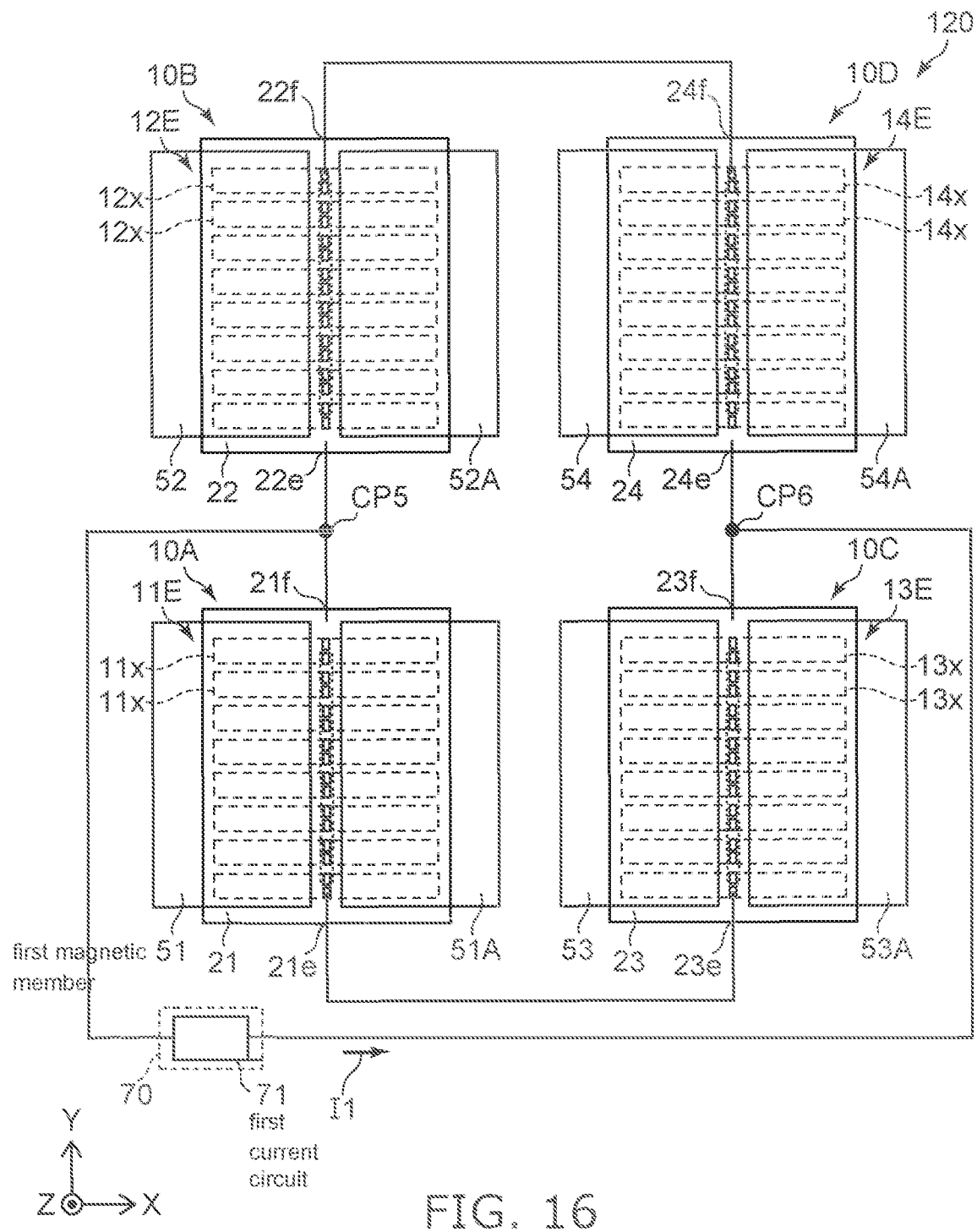
FIG. 16 is a schematic view illustrating the magnetic sensor according to the third embodiment.
Figure 17A:
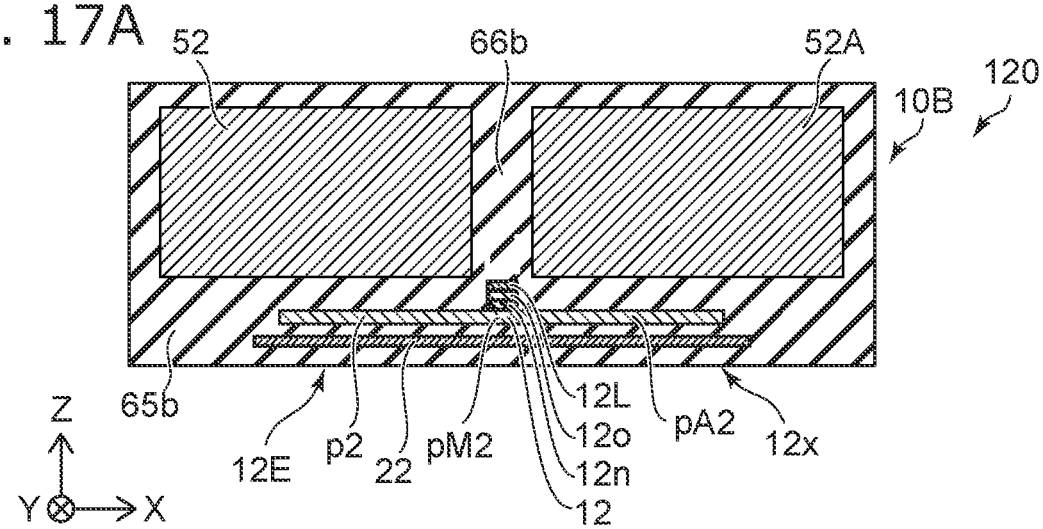
FIGS. 17A to 17C are schematic views illustrating the magnetic sensor according to the third embodiment.
Figure 17B:
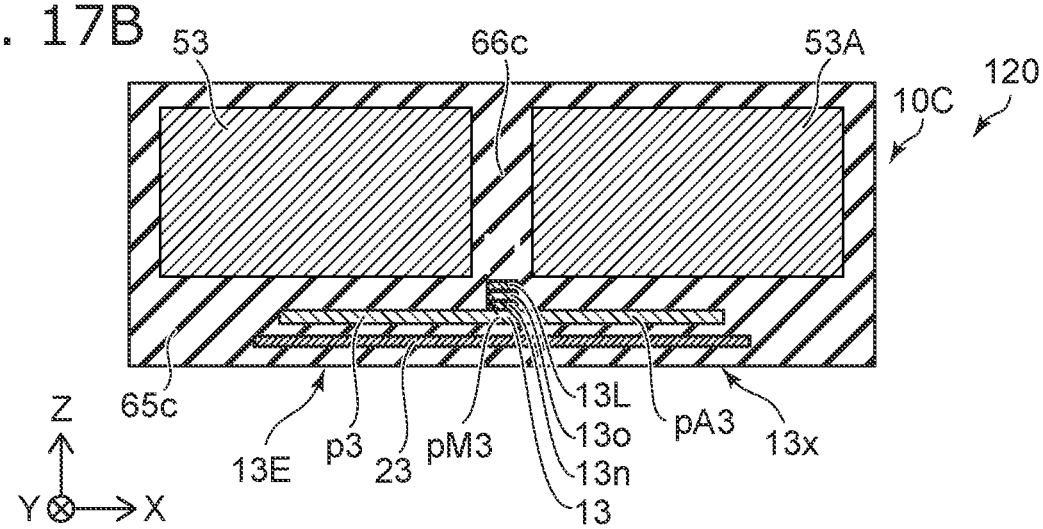
Figure 17C:
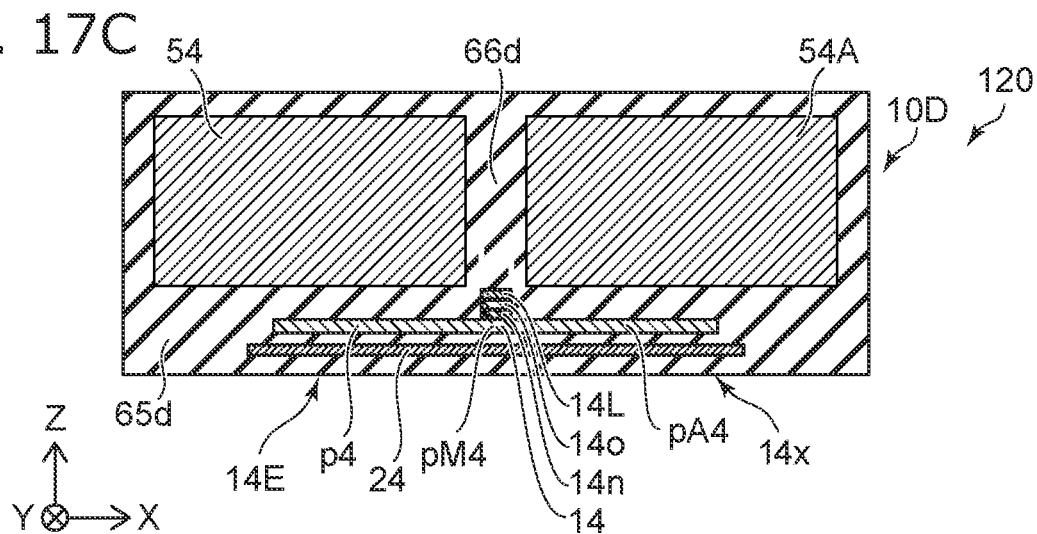

FIGS. 15 and 16 are plan views, FIGS. 17A to 17C are cross-sectional views.

As shown in FIG. 15, the magnetic sensor 120 according to the embodiment further includes a second sensor part 10B that includes a second magnetic element 12E, a third sensor part 10C that includes a third magnetic element 13E, a fourth sensor part 10D that includes a fourth magnetic element 14E, and the element current circuit 75 in addition to the first sensor part 10A that includes the first magnetic element 11E.

The second to fourth magnetic elements 12E to 14E each may have the configuration of the first magnetic element 11E. In the example, these magnetic elements have the configuration of the first magnetic element 11E of the magnetic sensor 113.

In the example, the one end 11Ee of the first magnetic element 11E is electrically connected with one end 13Ee of the third magnetic element 13E. The other end 11Ef of the first magnetic element 11E is electrically connected with one end 12Ee of the second magnetic element 12E. Another end 13Ef of the third magnetic element 13E is electrically connected with one end 14Ee of the fourth magnetic element 14E. Another end 12Ef of the second magnetic element 12E is electrically connected with another end 14Ef of the fourth magnetic element 14E.

As shown in FIG. 15, the element current circuit 75 is configured to supply the element current Id between a first connection point CP1 and a second connection point CP2, in which the first connection point CP1 is between the one end 11Ee of the first magnetic element 11E and the one end 13Ee of the third magnetic element 13E, and the second connection point CP2 is between the other end 12Ef of the second magnetic element 12E and the other end 14Ef of the fourth magnetic element 14E.

As shown in FIG. 15, the magnetic sensor 120 may further include a detection circuit 73. The detection circuit 73 is configured to detect the change of the potential between a third connection point CP3 and a fourth connection point CP4, in which the third connection point CP3 is between the other end 11Ef of the first magnetic element 11E and the one end 12Ee of the second magnetic element 12E, and the fourth connection point CP4 is between the other end 13Ef of the third magnetic element 13E and the one end 14Ee of the fourth magnetic element 14E.

The first to fourth magnetic elements 11E to 14E have a bridge connection. The change of the potential between two midpoints (the third connection point CP3 and the fourth connection point CP4) of the bridge circuit is detected by the detection circuit 73. The detection has higher sensitivity due to the bridge circuit.

As described above with reference to FIG. 7A, the first sensor part 10A includes the first conductive member 21. As shown in FIG. 7A, in the second direction (the Z-axis direction), at least a portion of the first conductive member 21 overlaps the region 66a between the first magnetic member 51 and the first counter magnetic member 51A.

As shown in FIG. 17A, the second sensor part 10B includes a second magnetic member 52, a second counter magnetic member 52A, and a second conductive member 22. In the second direction (the Z-axis direction), at least a portion of the second conductive member 22 overlaps a region 66b between the second magnetic member 52 and the second counter magnetic member 52A. The region 66b may be a portion of a second insulating member 65b.

As shown in FIG. 17B, the third sensor part 10C includes a third magnetic member 53, a third counter magnetic member 53A, and a third conductive member 23. In the second direction (the Z-axis direction), at least a portion of the third conductive member 23 overlaps a region 66c between the third magnetic member 53 and the third counter magnetic member 53A. The region 66c may be a portion of a third insulating member 65c.

As shown in FIG. 17C, the fourth sensor part 10D includes a fourth magnetic member 54, a fourth counter magnetic member 54A, and a fourth conductive member 24. In the second direction (the Z-axis direction), at least a portion of the fourth conductive member 24 overlaps a region 66d between the fourth magnetic member 54 and the fourth counter magnetic member 54A. The region 66d may be a portion of a fourth insulating member 65d.

As shown in FIG. 16, the one end 21e of the first conductive member 21 is electrically connected with one end 23e of the third conductive member 23. The other end 21f of the first conductive member 21 is electrically connected with one end 22e of the second conductive member 22. Another end 23f of the third conductive member 23 is electrically connected with one end 24e of the fourth conductive member 24. Another end 22f of the second conductive member 22 is electrically connected with another end 24f of the fourth conductive member 24.

As shown in FIG. 16, the first current circuit 71 is configured to supply the first current I1 that includes an alternating current component between a fifth connection point CP5 and a sixth connection point CP6, in which the fifth connection point CP5 is between the other end 21f of the first conductive member 21 and the one end 22e of the second conductive member 22, and the sixth connection point CP6 is between the other end 23f of the third conductive member 23 and the one end 24e of the fourth conductive member 24. Noise components are further suppressed by using the first current I1 that includes the alternating current component. Higher sensitivity is obtained.

According to the second embodiment, the relationship (the phase) between the orientation of the current flowing in the first magnetic element 11E and the orientation of the current flowing in the first conductive member 21 of the first sensor part 10A is opposite to the relationship (the phase) between the orientation of the current flowing in the third magnetic element 13E and the orientation of the current flowing in the third conductive member 23 of the third sensor part 10C. The relationship (the phase) between the orientation of the current flowing in the second magnetic element 12E and the orientation of the current flowing in the second conductive member 22 of the second sensor part 10B is opposite to the relationship (the phase) between the orientation of the current flowing in the fourth magnetic element 14E and the orientation of the current flowing in the fourth conductive member 24 of the fourth sensor part 10D. The relationship (the phase) between the orientation of the current flowing in the first magnetic element 11E and the orientation of the current flowing in the first conductive member 21 of the first sensor part 10A is opposite to the relationship (the phase) between the orientation of the current flowing in the second magnetic element 12E and the orientation of the current flowing in the second conductive member 22 of the second sensor part 10B.

For example, as shown in FIG. 17A, the direction from the second magnetic member 52 toward the second counter magnetic member 52A is along the first direction (the X-axis direction). The second magnetic element 12E includes one or multiple second extension parts 12x (referring to FIG. 15). As shown in FIG. 17A, the second extension part 12x includes a second magnetic layer 12, the second counter magnetic layer 12o, and the second nonmagnetic layer 12n. The second magnetic layer 12 includes a second portion p2, the second counter portion pA2, and the second middle portion pM2. The direction from the second portion p2 toward the second counter portion pA2 is along the second direction (the Z-axis direction). The second middle portion pM2 is between the second portion p2 and the second counter portion pA2. The second nonmagnetic layer 12n is between the second counter magnetic layer 12o and at least a portion of the second middle portion pM2 in the second direction.

For example, as shown in FIG. 17B, the direction from the third magnetic member 53 toward the third counter magnetic member 53A is along the first direction (the X-axis direction). The third magnetic element 13E includes due to one or multiple third extension parts 13x (referring to FIG. 15). As shown in FIG. 17B, the third extension part 13x includes a third magnetic layer 13, a third counter magnetic layer 13o, and a third nonmagnetic layer 13n. The third magnetic layer 13 includes a third portion p3, a third counter portion pA3, and a third middle portion pM3. The direction from the third portion p3 toward the third counter portion pA3 is along the second direction (the Z-axis direction). The third middle portion pM3 is between the third portion p3 and the third counter portion pA3. The third nonmagnetic layer 13n is between the third counter magnetic layer 13o and at least a portion of the third middle portion pM3 in the second direction.

For example, as shown in FIG. 17C, the direction from the fourth magnetic member 54 toward the fourth counter magnetic member 54A is along the first direction (the X-axis direction). The fourth magnetic element 14E includes one or multiple fourth extension parts 14x (referring to FIG. 15). As shown in FIG. 17C, the fourth extension part 14x includes a fourth magnetic layer 14, a fourth counter magnetic layer 14o, and a fourth nonmagnetic layer 14n. The fourth magnetic layer 14 includes a fourth portion p4, a fourth counter portion pA4, and a fourth middle portion pM4. The direction from the fourth portion p4 toward the fourth counter portion pA4 is along the second direction (the Z-axis direction). The fourth middle portion pM4 is between the fourth portion p4 and the fourth counter portion pA4. The fourth nonmagnetic layer 14n is between the fourth counter magnetic layer 14o and at least a portion of the fourth middle portion pM4 in the second direction.

Fourth Embodiment

A fourth embodiment relates to an inspection device. As described below, the inspection device may include a diagnostic device.

Figure 18:
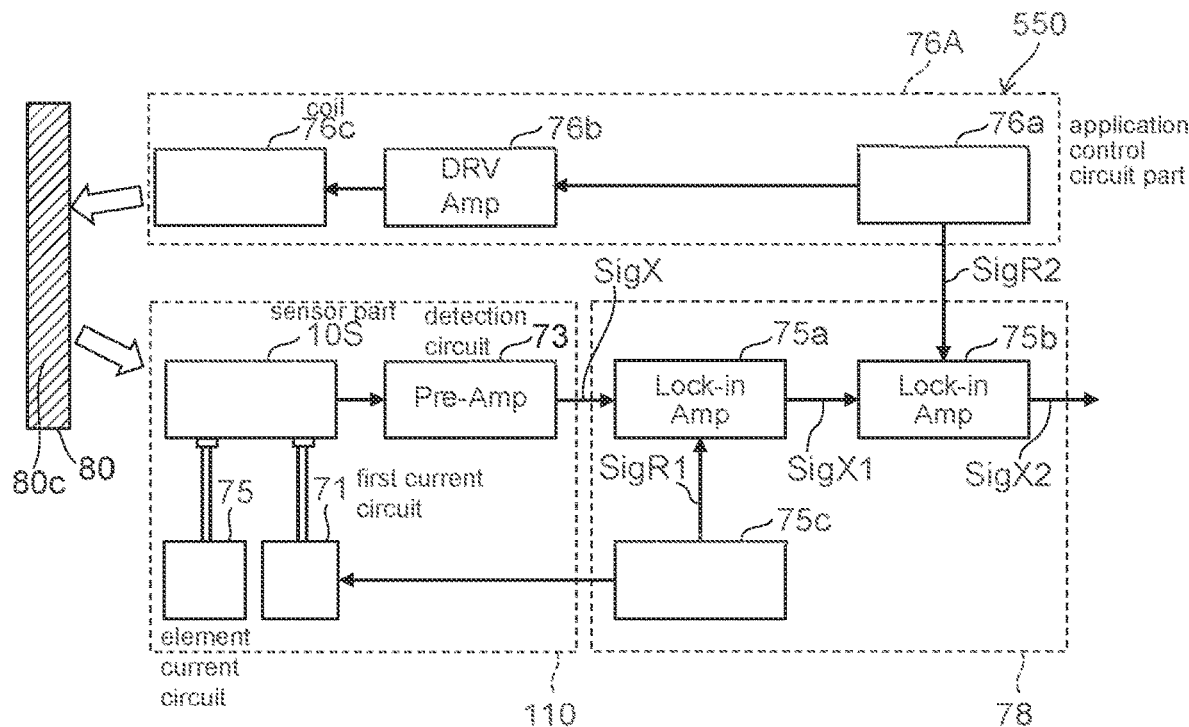
FIG. 18 is a schematic view illustrating an inspection device according to a fourth embodiment.

FIG. 18 is a schematic view illustrating the inspection device according to the fourth embodiment.

As shown in FIG. 18, the inspection device 550 according to the embodiment includes a processor 78 and the magnetic sensor (in the example of FIG. 18, the magnetic sensor 110) according to the embodiment. The processor 78 processes an output signal SigX obtained from the magnetic sensor 110. In the example, the processor 78 includes a sensor control circuit part 75c, a first lock-in amplifier 75a, and a second lock-in amplifier 75b. For example, the first current circuit 71 is controlled by the sensor control circuit part 75c; and the first current I1 that includes the alternating current component is supplied from the first current circuit 71 to a sensor part 10S. The frequency of the alternating current component of the first current I1 is, for example, not more than 100 kHz. The element current Id is supplied from the element current circuit 75 to the sensor part 10S. The sensor part 10S includes, for example, the first sensor part 10A, etc.

The sensor part 10S may include the first to fourth sensor parts 10A to 10D, etc. The change of the potential of the sensor part 10S is detected by the detection circuit 73. For example, the output of the detection circuit 73 is the output signal SigX.

In the example, the inspection device 550 includes a magnetic field application part 76A. The magnetic field application part 76A is configured to apply a magnetic field to a detection object 80. The detection object 80 is, for example, the inspection object. The detection object 80 includes at least an inspection conductive member 80c such as a metal, etc. For example, an eddy current is generated in the inspection conductive member 80c when the magnetic field due to the magnetic field application part 76A is applied to the inspection conductive member 80c. The state of the eddy current changes when there is a flaw or the like in the inspection conductive member 80c. The state (e.g., the flaw, etc.) of the inspection conductive member 80c can be inspected by the magnetic sensor (e.g., the magnetic sensor 110, etc.) detecting the magnetic field due to the eddy current. The magnetic field application part 76A is, for example, an eddy current generator.

In the example, the magnetic field application part 76A includes an application control circuit part 76a, a drive amplifier 76b, and a coil 76c. A current is supplied to the drive amplifier 76b by the control by the application control circuit part 76a. The current is, for example, an alternating current. The frequency of the current is, for example, an eddy current excitation frequency. The eddy current excitation frequency is, for example, not less than 10 Hz and not more than 100 kHz. The eddy current excitation frequency may be, for example, less than 100 kHz.

For example, information (which may be, for example, a signal) that relates to the frequency of the alternating current component of the first current I1 is supplied from the sensor control circuit part 75c to the first lock-in amplifier 75a as a reference wave (a reference signal). The output of the first lock-in amplifier 75a is supplied to the second lock-in amplifier 75b. Information (which may be, for example, a signal) that relates to the eddy current excitation frequency is supplied from the application control circuit part 76a to the second lock-in amplifier 75b as a reference wave (a reference signal). The second lock-in amplifier 75b is configured to output a signal component corresponding to the eddy current excitation frequency.

Thus, for example, the processor 78 includes the first lock-in amplifier 75a. The output signal SigX that is obtained from the magnetic sensor 110 and a signal SigR1 that corresponds to the frequency of the alternating current component included in the first current I1 are input to the first lock-in amplifier 75a. The first lock-in amplifier 75a is configured to output an output signal SigX1 that uses the signal SigR1 corresponding to the frequency of the alternating current component included in the first current I1 as a reference wave (a reference signal). By providing the first lock-in amplifier 75a, it is possible to suppress noise and detect with high sensitivity.

The processor 78 may further include the second lock-in amplifier 75b. The output signal SigX1 of the first lock-in amplifier 75a and a signal SigR2 that corresponds to the frequency (the eddy current excitation frequency) of the supply signal (in the example, the magnetic field due to the magnetic field application part 76A) supplied toward the detection object 80 (the inspection object) are input to the second lock-in amplifier 75b. The second lock-in amplifier 75b is configured to output an output signal SigX2 that uses the signal SigR2 corresponding to the frequency of the supply signal supplied toward the detection object 80 (the inspection object) as a reference wave (a reference signal). By providing the second lock-in amplifier 75b, it is possible to further suppress noise and detect with even higher sensitivity.

An abnormality such as a flaw or the like of the inspection conductive member 80c of the detection object 80 can be inspected by the inspection device 550.

Figure 19:
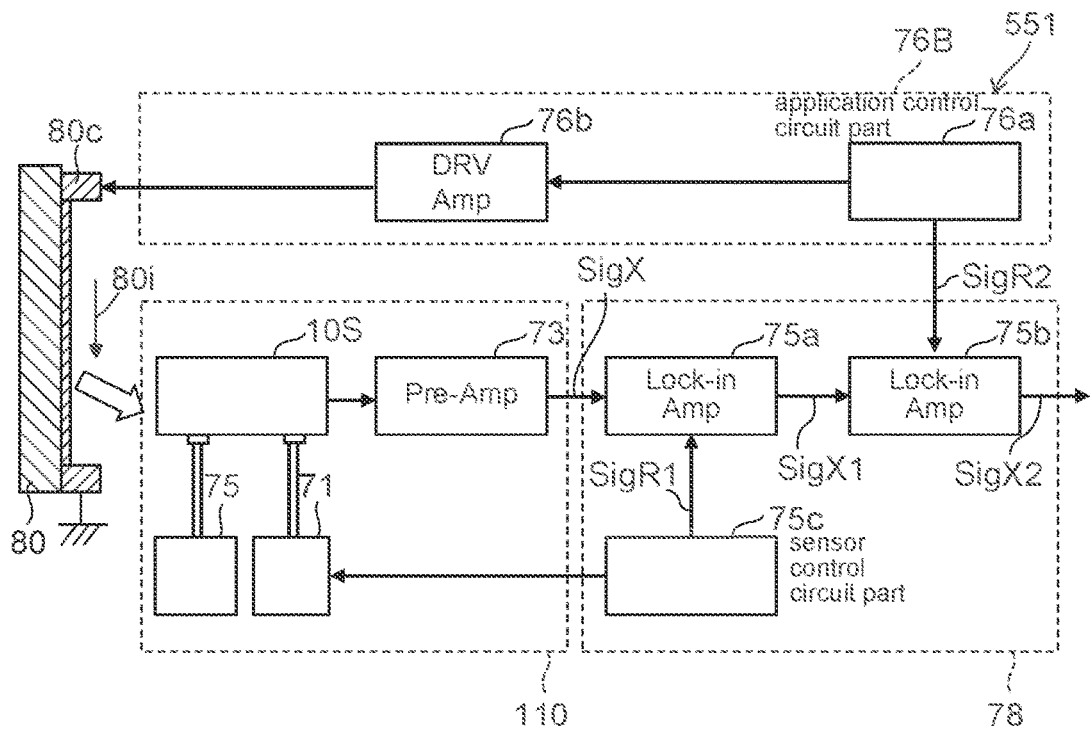
FIG. 19 is a schematic view illustrating an inspection device according to the third embodiment.

FIG. 19 is a schematic view illustrating an inspection device according to the third embodiment.

As shown in FIG. 19, the inspection device 551 according to the embodiment includes the processor 78 and the magnetic sensor (e.g., the magnetic sensor 110) according to the embodiment. The configurations of the magnetic sensor and the processor 78 of the inspection device 551 may be similar to those of the inspection device 550. In the example, the inspection device 551 includes a detection object driver 76B. The detection object driver 76B is configured to supply a current to the inspection conductive member 80c included in the detection object 80. The inspection conductive member 80c is, for example, wiring included in the detection object 80. A magnetic field that is due to a current 80i flowing in the inspection conductive member 80c is detected by the magnetic sensor 110. The inspection conductive member 80c can be inspected based on an abnormality due to the detection result of the magnetic sensor 110. The detection object 80 may be, for example, an electronic device such as a semiconductor device, etc. The detection object 80 may be, for example, a battery, etc.

In the example, the detection object driver 76B includes the application control circuit part 76a and the drive amplifier 76b. The drive amplifier 76b is controlled by the application control circuit part 76a; and a current is supplied from the drive amplifier 76b to the inspection conductive member 80c. The current is, for example, an alternating current. For example, the alternating current is supplied to the inspection conductive member 80c. The frequency of the alternating current is, for example, not less than 10 Hz and not more than 100 kHz. The frequency may be, for example, less than 100 kHz. In the example as well, for example, by providing the first lock-in amplifier 75a and the second lock-in amplifier 75b, it is possible to suppress noise and detect with high sensitivity. In one example of the inspection device 551, multiple magnetic sensors (e.g., the multiple magnetic sensors 110) may be provided. The multiple magnetic sensors are, for example, a sensor array. The inspection conductive member 80c can be inspected in a short period of time by the sensor array. In one example of the inspection device 551, the inspection conductive member 80c may be inspected by scanning the magnetic sensor (e.g., the magnetic sensor 110).

Figure 20:
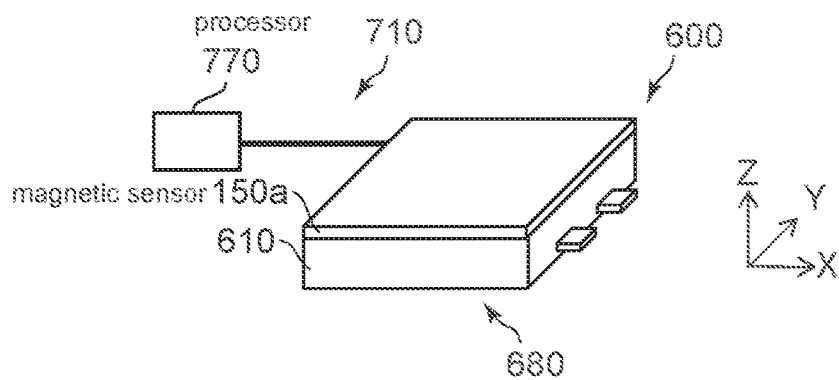
FIG. 20 is a schematic perspective view showing an inspection device according to the fourth embodiment.

FIG. 20 is a schematic perspective view showing an inspection device according to the fourth embodiment.

As shown in FIG. 20, the inspection device 710 according to the embodiment includes a magnetic sensor 150a and a processor 770. The magnetic sensor 150a may be the magnetic sensor according to one of the first to third embodiments or a modification of the magnetic sensor. The processor 770 processes an output signal obtained from the magnetic sensor 150a. The processor 770 may perform a comparison between a reference value and the signal obtained from the magnetic sensor 150a, etc. The processor 770 is configured to output an inspection result based on the processing result.

For example, an inspection object 680 is inspected by the inspection device 710. The inspection object 680 is, for example, an electronic device (including a semiconductor circuit, etc.). The inspection object 680 may be, for example, a battery 610, etc.

For example, the magnetic sensor 150a according to the embodiment may be used together with the battery 610. For example, a battery system 600 includes the battery 610 and the magnetic sensor 150a. The magnetic sensor 150a can detect a magnetic field generated by a current flowing in the battery 610.

Figure 21:
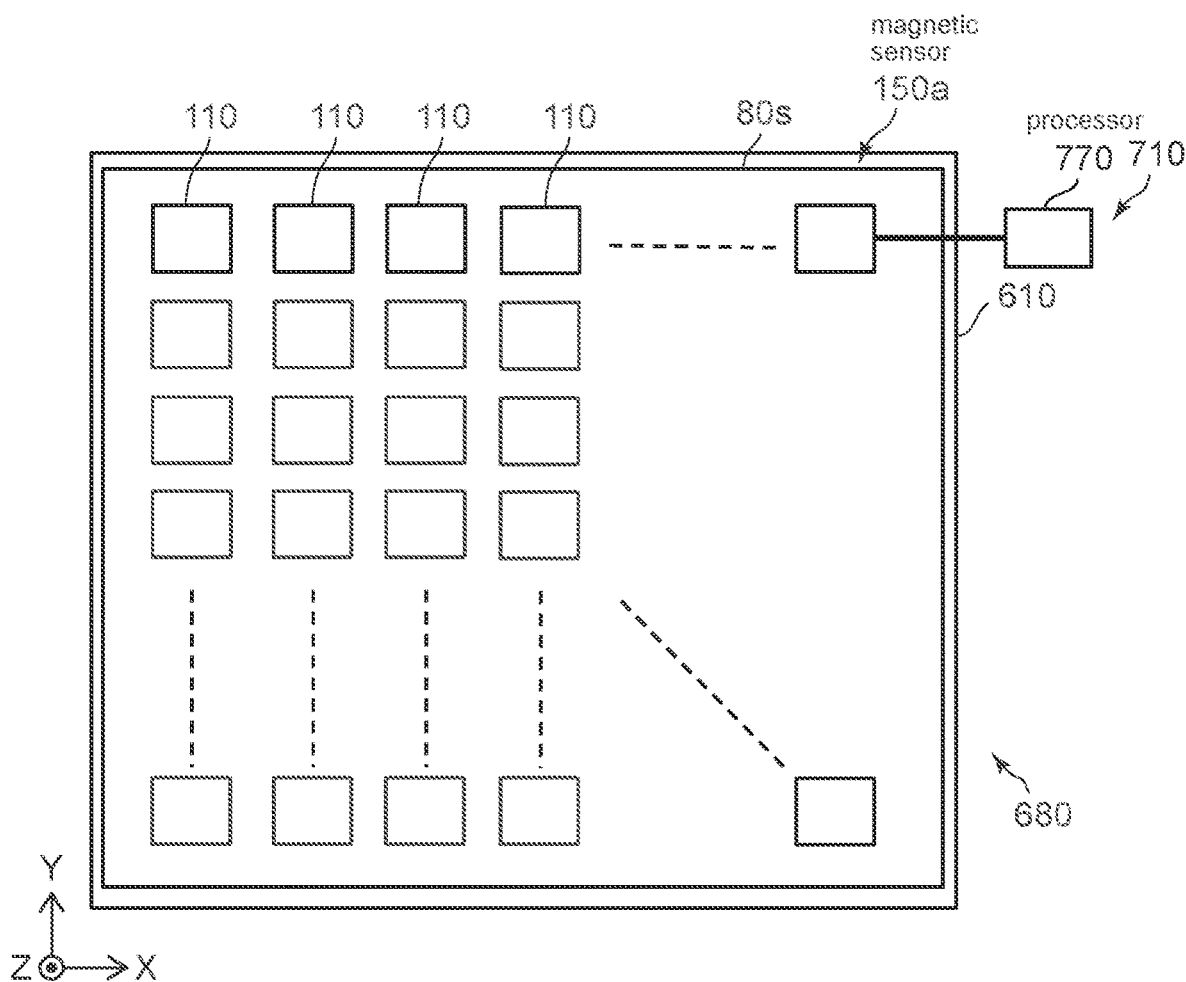
FIG. 21 is a schematic plan view showing the inspection device according to the fourth embodiment.

FIG. 21 is a schematic plan view showing the inspection device according to the fourth embodiment.

As shown in FIG. 21, the magnetic sensor 150a includes, for example, multiple magnetic sensors according to the embodiment. In the example, the magnetic sensor 150a includes multiple magnetic sensors (e.g., the magnetic sensor 110, etc.). For example, the multiple magnetic sensors are arranged along two directions (e.g., the X-axis direction and the Y-axis direction). For example, the multiple magnetic sensors 110 are located on a substrate.

The magnetic sensor 150a can detect a magnetic field generated by a current flowing in the inspection object 680 (which may be, for example, the battery 610). For example, an abnormal current flows in the battery 610 when the battery 610 approaches an abnormal state. The change of the state of the battery 610 can be known by the magnetic sensor 150a detecting the abnormal current. For example, the entire battery 610 can be inspected in a short period of time by moving the sensor array in two directions while the magnetic sensor 150a is proximate to the battery 610. The magnetic sensor 150a may be used to inspect the battery 610 in the manufacturing process of the battery 610.

Figure 22:
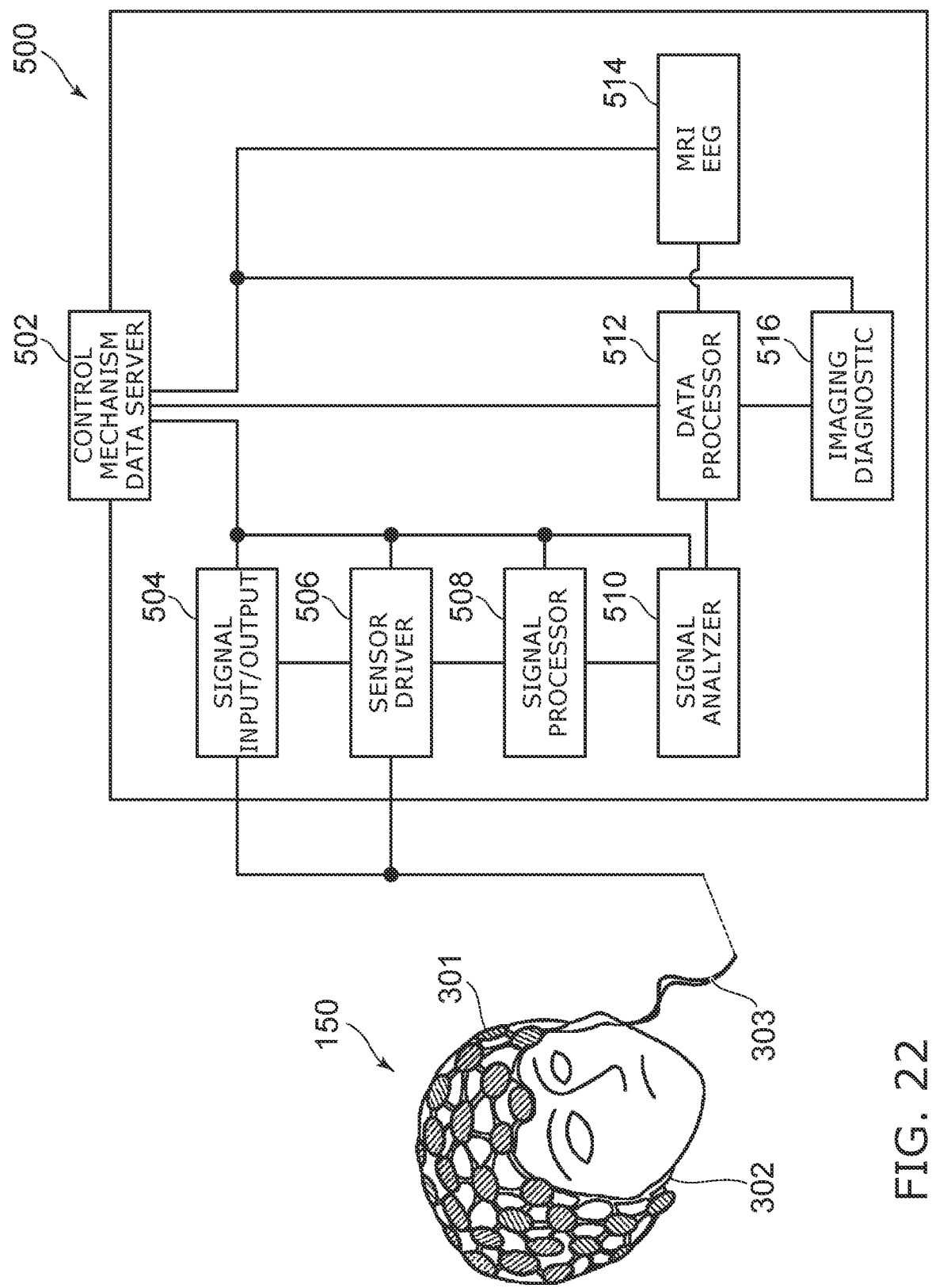
FIG. 22 is a schematic view showing the magnetic sensor and the inspection device according to the fourth embodiment.

For example, the magnetic sensor according to the embodiment is applicable to the inspection device 710 such as a diagnostic device, etc. FIG. 22 is a schematic view showing the magnetic sensor and the inspection device according to the fourth embodiment.

As shown in FIG. 22, the diagnostic device 500 is an example of the inspection device 710 and includes the magnetic sensor 150. The magnetic sensor 150 includes the magnetic sensors described in reference to the first to fifth embodiments and modifications of the magnetic sensors.

In the diagnostic device 500, the magnetic sensor 150 is, for example, a magnetoencephalography device. The magnetoencephalography device detects a magnetic field generated by cranial nerves. When the magnetic sensor 150 is included in a magnetoencephalography device, the size of the magnetic element included in the magnetic sensor 150 is, for example, not less than 1 mm but less than 10 mm. The size is, for example, the length including the MFC.

As shown in FIG. 22, the magnetic sensor 150 (the magnetoencephalography device) is mounted to, for example, the head of a human body. The magnetic sensor 150 (the magnetoencephalography device) includes a sensor part 301. The magnetic sensor 150 (the magnetoencephalography device) may include multiple sensor parts 301. The number of the multiple sensor parts 301 is, for example, about 100 (e.g., not less than 50 and not more than 150). The multiple sensor parts 301 are provided on a flexible base body 302.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 is small compared to the size of a conventional SQUID magnetic sensor. Therefore, the mounting of the multiple sensor parts 301 is easy. The mounting of the multiple sensor parts 301 and the other circuits is easy. The multiple sensor parts 301 and the other sensors can be easily mounted together.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected with a sensor driver 506 and a signal input/output part 504 of the diagnostic device 500. A magnetic field measurement is performed in the sensor part 301 based on electrical power from the sensor driver 506 and a control signal from the signal input/output part 504. The result is input to the signal input/output part 504. The signal that is obtained by the signal input/output part 504 is supplied to a signal processor 508. Processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as EEG (Electroencephalogram), etc., in the data analysis. For example, a data part 514 of the MRI, the EEG, etc., is connected with the data processor 512. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, or the like is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 22, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be flexible or may be substantially not flexible. In the example shown in FIG. 22, the base body 302 is a continuous membrane that is patterned into a hat-like configuration. The base body 302 may have a net configuration. For example, a good fit is obtained thereby. For example, the adhesion of the base body 302 to the human body is improved. The base body 302 may have a hard helmet-like configuration.

Figure 23:
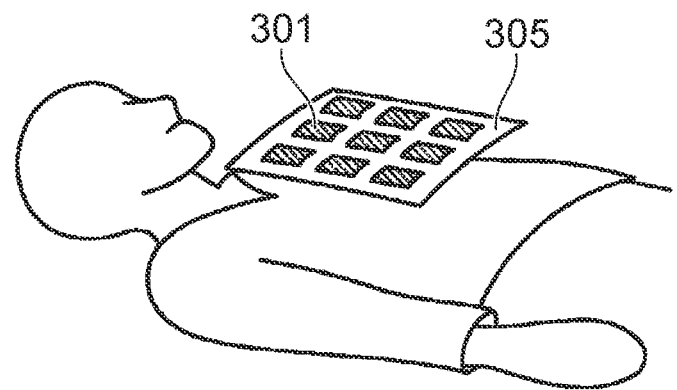
FIG. 23 is a schematic view showing the inspection device according to the fourth embodiment.

FIG. 23 is a schematic view showing the inspection device according to the fourth embodiment.

FIG. 23 is an example of a magnetic detection instrument. In the example, the sensor part 301 is provided on a hard base body 305 having a flat plate shape.

The input and output of the signal obtained from the sensor part 301 in the example shown in FIG. 23 are similar to the input and output described with reference to FIG. 22. The processing of the signal obtained from the sensor part 301 in the example shown in FIG. 23 is similar to the processing described with reference to FIG. 22.

There is a reference example in which a SQUID (Superconducting Quantum Interference Device) magnetic sensor is used as a device to measure a faint magnetic field such as a magnetic field emitted from a living body, etc. Because superconductivity is used in the reference example, the device is large; and the power consumption is large. The load on the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:
a first sensor part including
a first magnetic member,
a first counter magnetic member, a direction from the first magnetic member toward the first counter magnetic member being along a first direction, and
a first magnetic element including one or a plurality of first extension parts,
the first extension part including a first magnetic layer, a first counter magnetic layer, and a first nonmagnetic layer,
the first magnetic layer including a first portion, a first counter portion, and a first middle portion,
a direction from the first portion toward the first counter portion being along the first direction,
the first middle portion being between the first portion and the first counter portion,
the first nonmagnetic layer being between the first counter magnetic layer and at least a portion of the first middle portion in a second direction crossing the first direction.

Configuration 2

The magnetic sensor according to Configuration 1, wherein
a position in the first direction of the first nonmagnetic layer is between a position in the first direction of the first magnetic member and a position in the first direction of the first counter magnetic member.

Configuration 3

The magnetic sensor according to Configuration 1 or 2, wherein
the first sensor part further includes a first insulating member, and at least a portion of the first insulating member is between the first portion and the first magnetic member and between the first counter portion and the first counter magnetic member.

Configuration 4

The magnetic sensor according to any one of Configurations 1 to 3, wherein a first magnetic layer length along the first direction of the first magnetic layer is not less than 2 times a first distance, and the first distance is along the first direction between the first magnetic member and the first counter magnetic member.

Configuration 5

The magnetic sensor according to Configuration 4, wherein a first nonmagnetic layer length along the first direction of the first nonmagnetic layer is not more than the first distance.

Configuration 6

The magnetic sensor according to any one of Configurations 1 to 5, wherein the first extension part further includes a first layer, the first layer includes at least one selected from the group consisting of IrMn and PtMn, the first counter magnetic layer is located between the first magnetic layer and the first layer, and the first nonmagnetic layer includes MgO.

Configuration 7

The magnetic sensor according to any one of Configurations 1 to 6, wherein the first sensor part includes a first conductive member, in the second direction, at least a portion of the first conductive member overlaps a region between the first magnetic member and the first counter magnetic member, a first current includes an alternating current component and can flow in the first conductive member, the first current flows through the first conductive member along a third direction, and the third direction crosses a plane including the first and second directions.

Configuration 8

The magnetic sensor according to any one of Configurations 1 to 7, wherein an electrical resistance of the first magnetic element has an even-function characteristic with respect to a magnetic field applied to the first magnetic element.

Configuration 9

The magnetic sensor according to any one of Configurations 1 to 8, wherein an electrical resistance of the first magnetic element has a first value when a first magnetic field is applied to the first magnetic element, the electrical resistance has a second value when a second magnetic field is applied to the first magnetic element, the electrical resistance has a third value when a third magnetic field is applied to the first magnetic element, an absolute value of the first magnetic field is less than an absolute value of the second magnetic field and less than an absolute value of the third magnetic field, an orientation of the second magnetic field is opposite to an orientation of the third magnetic field, and the first value is less than the second value and less than the third value.

Configuration 10

The magnetic sensor according to any one of Configurations 1 to 9, wherein the first extension part includes a second counter magnetic layer and a second nonmagnetic layer, the first nonmagnetic layer is between the first counter magnetic layer and a portion of the first middle portion in the second direction, the second nonmagnetic layer is between the second counter magnetic layer and an other portion of the first middle portion in the second direction, and a direction from the second nonmagnetic layer toward the first nonmagnetic layer is along a third direction crossing a plane including the first and second directions.

Configuration 11

The magnetic sensor according to Configuration 10, wherein the first magnetic element includes the plurality of first extension parts, and the plurality of first extension parts is arranged along a third direction crossing a plane including the first and second directions.

Configuration 12

The magnetic sensor according to Configuration 11, wherein a direction from the first nonmagnetic layer of one of the plurality of first extension parts toward the first nonmagnetic layer of an other one of the plurality of first extension parts is along the third direction.

Configuration 13

The magnetic sensor according to Configuration 11 or 12, wherein the first magnetic element further includes a first connection member, and the first connection member electrically connects the second counter magnetic layer of one of the plurality of first extension parts and the first counter magnetic layer of an other one of the plurality of first extension parts.

Configuration 14

The magnetic sensor according to any one of Configurations 1 to 13, wherein the first sensor part further includes an other first counter magnetic member, the first counter magnetic member is between the first magnetic member and the other first counter magnetic member in the first direction, the first extension part further includes a second counter magnetic layer and a second nonmagnetic layer, the first magnetic layer further includes a second counter portion and a second middle portion, the first counter portion is between the first portion and the second counter portion in the first direction, the second middle portion is between the first counter portion and the second counter portion, and the second nonmagnetic layer is between the second counter magnetic layer and at least a portion of the second middle portion in the second direction.

Configuration 15

The magnetic sensor according to Configuration 14, wherein the first magnetic element includes the plurality of first extension parts and a first connection member, the plurality of first extension parts is arranged along a third direction crossing a plane including the first and second directions, and the first connection member electrically connects the second counter magnetic layer of one of the plurality of first extension parts and the second counter magnetic layer of another one of the plurality of first extension parts.

Configuration 16

The magnetic sensor according to any one of Configurations 1 to 9, further comprising:
a second sensor part including a second magnetic element,
a third sensor part including a third magnetic element,
a fourth sensor part including a fourth magnetic element, and
an element current circuit,
one end of the first magnetic element being electrically connected with one end of the third magnetic element,
an other end of the first magnetic element being electrically connected with one end of the second magnetic element,
an other end of the third magnetic element being electrically connected with one end of the fourth magnetic element,
an other end of the second magnetic element being electrically connected with an other end of the fourth magnetic element,
the element current circuit being configured to supply an element current between a first connection point and a second connection point,
the first connection point being between the one end of the first magnetic element and the one end of the third magnetic element,
the second connection point being between the other end of the second magnetic element and the other end of the fourth magnetic element.

Configuration 17

The magnetic sensor according to Configuration 16, further comprising:
a detection circuit,
the detection circuit being configured to detect a change of a potential between a third connection point and a fourth connection point,
the third connection point being between the other end of the first magnetic element and the one end of the second magnetic element,
the fourth connection point being between the other end of the third magnetic element and the one end of the fourth magnetic element.

Configuration 18

The magnetic sensor according to Configuration 16 or 17, further comprising:
a first current circuit,
the first sensor part including a first conductive member,
in the second direction, at least a portion of the first conductive member overlapping a region between the first magnetic member and the first counter magnetic member,
the second sensor part including a second magnetic member, a second counter magnetic member, and a second conductive member,
in the second direction, at least a portion of the second conductive member overlapping a region between the second magnetic member and the second counter magnetic member,
the third sensor part including a third magnetic member, a third counter magnetic member, and a third conductive member,
in the second direction, at least a portion of the third conductive member overlapping a region between the third magnetic member and the third counter magnetic member,
the fourth sensor part including a fourth magnetic member, a fourth counter magnetic member, and a fourth conductive member,
in the second direction, at least a portion of the fourth conductive member overlapping a region between the fourth magnetic member and the fourth counter magnetic member,
one end of the first conductive member being electrically connected with one end of the third conductive member,
an other end of the first conductive member being electrically connected with one end of the second conductive member,
an other end of the third conductive member being electrically connected with one end of the fourth conductive member,
an other end of the second conductive member being electrically connected with an other end of the fourth conductive member,
the first current circuit being configured to supply a first current between a fifth connection point and a sixth connection point,
the first current including an alternating current component,
the fifth connection point being between the other end of the first conductive member and the one end of the second conductive member,
the sixth connection point being between the other end of the third conductive member and the one end of the fourth conductive member.

Configuration 19

The magnetic sensor according to any one of Configurations 16 to 18, wherein
the second sensor part includes:
a second magnetic member; and
a second counter magnetic member,
a direction from the second magnetic member toward the second counter magnetic member is along the first direction,
the second magnetic element includes one or a plurality of second extension parts,
the second extension part includes a second magnetic layer, a second counter magnetic layer, and a second nonmagnetic layer,
the second magnetic layer includes a second portion, a second counter portion, and a second middle portion,
a direction from the second portion toward the second counter portion is along the second direction,
the second middle portion is between the second portion and the second counter portion,
the second nonmagnetic layer is between the second counter magnetic layer and at least a portion of the second middle portion in the second direction,
the third sensor part includes:
a third magnetic member; and
a third counter magnetic member,
a direction from the third magnetic member toward the third counter magnetic member is along the first direction,
the third magnetic element includes one or a plurality of third extension parts,
the third extension part includes a third magnetic layer, a third counter magnetic layer, and a third nonmagnetic layer,
the third magnetic layer includes a third portion, a third counter portion, and a third middle portion,
a direction from the third portion toward the third counter portion is along the second direction,
the third middle portion is between the third portion and the third counter portion, the third nonmagnetic layer is between the third counter magnetic layer and at least a portion of the third middle portion in the second direction, the fourth sensor part includes:
a fourth magnetic member; and
a fourth counter magnetic member,
a direction from the fourth magnetic member toward the fourth counter magnetic member is along the first direction,
the fourth magnetic element includes one or a plurality of fourth extension parts,
the fourth extension part includes a fourth magnetic layer, a fourth counter magnetic layer, and a fourth nonmagnetic layer,
the fourth magnetic layer includes a fourth portion, a fourth counter portion, and a fourth middle portion,
a direction from the fourth portion toward the fourth counter portion is along the second direction,
the fourth middle portion is between the fourth portion and the fourth counter portion,
the fourth nonmagnetic layer is between the fourth counter magnetic layer and at least a portion of the fourth middle portion in the second direction.

Configuration 20

An inspection device, comprising:
the magnetic sensor according to any one of Configurations 1 to 19; and
a processor configured to process a signal output from the magnetic sensor.

According to embodiments, a magnetic sensor and an inspection device can be provided in which the sensitivity can be increased.

In the specification of the application, "perpendicular" and "parallel" refer to not only strictly perpendicular and strictly parallel but &so include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as sensor parts, magnetic elements, magnetic layers, nonmagnetic layers, magnetic members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
a first sensor part including
a first magnetic member,
a first counter magnetic member, a direction from the first magnetic member toward the first counter magnetic member being along a first direction, and
a first magnetic element including one or a plurality of first extension parts,
the first extension part including a first magnetic layer, a first counter magnetic layer, and a first nonmagnetic layer,
the first magnetic layer including a first portion, a first counter portion, and a first middle portion,
a direction from the first portion toward the first counter portion being along the first direction,
the first middle portion being between the first portion and the first counter portion,
the first nonmagnetic layer being between the first counter magnetic layer and at least a portion of the first middle portion in a second direction crossing the first direction,
wherein
an electrical resistance of the first magnetic element has a first value when a first magnetic field is applied to the first magnetic element,
the electrical resistance has a second value when a second magnetic field is applied to the first magnetic element,
the electrical resistance has a third value when a third magnetic field is applied to the first magnetic element,
an absolute value of the first magnetic field is less than an absolute value of the second magnetic field and less than an absolute value of the third magnetic field,
an orientation of the second magnetic field is opposite to an orientation of the third magnetic field, and
the first value is less than the second value and less than the third value.

2. The sensor according to claim 1, wherein
a position in the first direction of the first nonmagnetic layer is between a position in the first direction of the first magnetic member and a position in the first direction of the first counter magnetic member.

3. The sensor according to claim 1, wherein
the first sensor part further includes a first insulating member, and
at least a portion of the first insulating member is between the first portion and the first magnetic member and between the first counter portion and the first counter magnetic member.

4. The sensor according to claim 1, wherein
a first magnetic layer length along the first direction of the first magnetic layer is not less than 2 times a first distance, and
the first distance is along the first direction between the first magnetic member and the first counter magnetic member.

5. The sensor according to claim 4, wherein
a first nonmagnetic layer length along the first direction of the first nonmagnetic layer is not more than the first distance.

6. The sensor according to claim 1, wherein
the first extension part further includes a first layer,
the first layer includes at least one selected from the group consisting of IrMn and PtMn,
the first counter magnetic layer is located between the first magnetic layer and the first layer, and
the first nonmagnetic layer includes MgO.

7. The sensor according to claim 1, wherein
the first sensor part includes a first conductive member,
in the second direction, at least a portion of the first conductive member overlaps a region between the first magnetic member and the first counter magnetic member,
a first current includes an alternating current component and can flow in the first conductive member,
the first current flows through the first conductive member along a third direction, and
the third direction crosses a plane including the first and second directions.

8. The sensor according to claim 1, wherein
an electrical resistance of the first magnetic element has an even-function characteristic with respect to a magnetic field applied to the first magnetic element.

9. The sensor according to claim 1, wherein
the first extension part includes a second counter magnetic layer and a second nonmagnetic layer,
the first nonmagnetic layer is between the first counter magnetic layer and a portion of the first middle portion in the second direction, and
the second nonmagnetic layer is between the second counter magnetic layer and an other portion of the first middle portion in the second direction.

10. The sensor according to claim 9, wherein
the first magnetic element includes the plurality of first extension parts.

11. The sensor according to claim 10, wherein
the first magnetic element further includes a first connection member, and
the first connection member electrically connects the second counter magnetic layer of one of the plurality of first extension parts and the first counter magnetic layer of an other one of the plurality of first extension parts.

12. An inspection device, comprising:
the magnetic sensor according to claim 1; and
a processor configured to process a signal output from the magnetic sensor.

13. A magnetic sensor, comprising:
a first sensor part including
a first magnetic member,
a first counter magnetic member, a direction from the first magnetic member toward the first counter magnetic member being along a first direction, and
a first magnetic element including one or a plurality of first extension parts,
the first extension part including a first magnetic layer, a first counter magnetic layer, and a first nonmagnetic layer,
the first magnetic layer including a first portion, a first counter portion, and a first middle portion,
a direction from the first portion toward the first counter portion being along the first direction,
the first middle portion being between the first portion and the first counter portion,
the first nonmagnetic layer being between the first counter magnetic layer and at least a portion of the first middle portion in a second direction crossing the first direction;
wherein
the first sensor part further includes an other first counter magnetic member,
the first counter magnetic member is between the first magnetic member and the other first counter magnetic member in the first direction,
the first extension part further includes a second counter magnetic layer and a second nonmagnetic layer,
the first magnetic layer further includes a second counter portion and a second middle portion,
the first counter portion is between the first portion and the second counter portion in the first direction,
the second middle portion is between the first counter portion and the second counter portion, and
the second nonmagnetic layer is between the second counter magnetic layer and at least a portion of the second middle portion in the second direction.

14. The sensor according to claim 13, wherein
the first magnetic element includes the plurality of first extension parts and a first connection member,
the plurality of first extension parts is arranged along a third direction crossing a plane including the first and second directions, and
the first connection member electrically connects the second counter magnetic layer of one of the plurality of first extension parts and the second counter magnetic layer of an other one of the plurality of first extension parts.

15. A magnetic sensor, comprising:
a first sensor part including
a first magnetic member,
a first counter magnetic member, a direction from the first magnetic member toward the first counter magnetic member being along a first direction, and
a first magnetic element including one or a plurality of first extension parts,
a second sensor part including a second magnetic element,
a third sensor part including a third magnetic element,
a fourth sensor part including a fourth magnetic element, and
an element current circuit,
the first extension part including a first magnetic layer, a first counter magnetic layer, and a first nonmagnetic layer,
the first magnetic layer including a first portion, a first counter portion, and a first middle portion,
a direction from the first portion toward the first counter portion being along the first direction,
the first middle portion being between the first portion and the first counter portion,
the first nonmagnetic layer being between the first counter magnetic layer and at least a portion of the first middle portion in a second direction crossing the first direction,
one end of the first magnetic element being electrically connected with one end of the third magnetic element,
an other end of the first magnetic element being electrically connected with one end of the second magnetic element,
an other end of the third magnetic element being electrically connected with one end of the fourth magnetic element, an other end of the second magnetic element being electrically connected with an other end of the fourth magnetic element, the element current circuit being configured to supply an element current between a first connection point and a second connection point, the first connection point being between the one end of the first magnetic element and the one end of the third magnetic element, the second connection point being between the other end of the second magnetic element and the other end of the fourth magnetic element.

16. The sensor according to claim 15, further comprising:
a detection circuit,
the detection circuit being configured to detect a change of a potential between a third connection point and a fourth connection point,
the third connection point being between the other end of the first magnetic element and the one end of the second magnetic element,
the fourth connection point being between the other end of the third magnetic element and the one end of the fourth magnetic element.

17. The sensor according to claim 15, further comprising:
a first current circuit,
the first sensor part including a first conductive member,
in the second direction, at least a portion of the first conductive member overlapping a region between the first magnetic member and the first counter magnetic member,
the second sensor part including a second magnetic member, a second counter magnetic member, and a second conductive member,
in the second direction, at least a portion of the second conductive member overlapping a region between the second magnetic member and the second counter magnetic member,
the third sensor part including a third magnetic member, a third counter magnetic member, and a third conductive member,
in the second direction, at least a portion of the third conductive member overlapping a region between the third magnetic member and the third counter magnetic member,
the fourth sensor part including a fourth magnetic member, a fourth counter magnetic member, and a fourth conductive member,
in the second direction, at least a portion of the fourth conductive member overlapping a region between the fourth magnetic member and the fourth counter magnetic member,
one end of the first conductive member being electrically connected with one end of the third conductive member,
an other end of the first conductive member being electrically connected with one end of the second conductive member,
an other end of the third conductive member being electrically connected with one end of the fourth conductive member,
an other end of the second conductive member being electrically connected with an other end of the fourth conductive member,
the first current circuit being configured to supply a first current between a fifth connection point and a sixth connection point,
the first current including an alternating current component,
the fifth connection point being between the other end of the first conductive member and the one end of the second conductive member,
the sixth connection point being between the other end of the third conductive member and the one end of the fourth conductive member.

18. The sensor according to claim 15, wherein
the second sensor part includes:
a second magnetic member; and
a second counter magnetic member,
a direction from the second magnetic member toward the second counter magnetic member being along the first direction,
the second magnetic element includes one or a plurality of second extension parts,
the second extension part includes a second magnetic layer, a second counter magnetic layer, and a second nonmagnetic layer,
the second magnetic layer includes a second portion, a second counter portion, and a second middle portion,
a direction from the second portion toward the second counter portion being along the second direction,
the second middle portion is between the second portion and the second counter portion,
the second nonmagnetic layer is between the second counter magnetic layer and at least a portion of the second middle portion in the second direction,
the third sensor part includes:
a third magnetic member; and
a third counter magnetic member,
a direction from the third magnetic member toward the third counter magnetic member being along the first direction,
the third magnetic element includes one or a plurality of third extension parts,
the third extension part includes a third magnetic layer, a third counter magnetic layer, and a third nonmagnetic layer,
the third magnetic layer includes a third portion, a third counter portion, and a third middle portion,
a direction from the third portion toward the third counter portion being along the second direction,
the third middle portion is between the third portion and the third counter portion,
the third nonmagnetic layer is between the third counter magnetic layer and at least a portion of the third middle portion in the second direction,
the fourth sensor part includes:
a fourth magnetic member; and
a fourth counter magnetic member,
a direction from the fourth magnetic member toward the fourth counter magnetic member being along the first direction,
the fourth magnetic element includes one or a plurality of fourth extension parts,
the fourth extension part includes a fourth magnetic layer, a fourth counter magnetic layer, and a fourth nonmagnetic layer,
the fourth magnetic layer includes a fourth portion, a fourth counter portion, and a fourth middle portion,
a direction from the fourth portion toward the fourth counter portion being along the second direction,
the fourth middle portion is between the fourth portion and the fourth counter portion, the fourth nonmagnetic layer is between the fourth counter magnetic layer and at least a portion of the fourth middle portion in the second direction.

19. A magnetic sensor, comprising:
a first sensor part including
a first magnetic member,
a first counter magnetic member, a direction from the first magnetic member toward the first counter magnetic member being along a first direction, and
a first magnetic element including one or a plurality of first extension parts,
the first extension part including a first magnetic layer, a first counter magnetic layer, and a first nonmagnetic layer,
the first magnetic layer including a first portion, a first counter portion, and a first middle portion,
a direction from the first portion toward the first counter portion being along the first direction,
the first middle portion being between the first portion and the first counter portion,
the first nonmagnetic layer being between the first counter magnetic layer and at least a portion of the first middle portion in a second direction crossing the first direction,
an area of the first magnetic layer in a plane perpendicular to the second direction being larger than an area of the first counter magnetic layer in the plane.

* * * * *